United States Patent [19]
Knutzon

[11] Patent Number: 6,051,754
[45] Date of Patent: Apr. 18, 2000

[54] METHODS AND COMPOSITIONS FOR SYNTHESIS OF LONG CHAIN POLY-UNSATURATED FATTY ACIDS IN PLANTS

[75] Inventor: Deborah Knutzon, Granite Bay, Calif.

[73] Assignees: Abbott Laboratories, Abbott Park, Ill.; Calgene, LLC, Davis, Calif.

[21] Appl. No.: 08/956,985

[22] Filed: Oct. 24, 1997

Related U.S. Application Data

[63] Continuation-in-part of application No. 08/834,033, Apr. 11, 1997, and a continuation-in-part of application No. 08/833,610, Apr. 11, 1997, Pat. No. 5,972,664.

[51] Int. Cl.$^7$ .............................. C12N 15/82; C12N 5/04; C07H 21/04
[52] U.S. Cl. ..................... 800/281; 536/23.2; 435/252.3; 435/419
[58] Field of Search .......................... 536/23.2; 435/134, 435/419, 468, 471, 430, 252.3; 800/281, 298

[56] References Cited

U.S. PATENT DOCUMENTS

| | | | |
|---|---|---|---|
| 3,649,295 | 3/1972 | Bernhart | 99/57 |
| 4,058,594 | 11/1977 | Williiams | 424/37 |
| 4,526,793 | 7/1985 | Ingenbleek et al. | 426/72 |
| 4,526,902 | 7/1985 | Rubin | 514/560 |
| 4,614,663 | 9/1986 | Rule | 426/601 |
| 4,670,285 | 6/1987 | Clandinin et al. | 426/602 |
| 4,843,095 | 6/1989 | Rubin | 514/558 |
| 4,920,098 | 4/1990 | Cotter et al. | 514/2 |
| 4,938,984 | 7/1990 | Traitler et al. | 426/580 |
| 5,057,419 | 10/1991 | Martin et al. | 435/134 |
| 5,374,657 | 12/1994 | Kyle | 514/547 |
| 5,376,541 | 12/1994 | Kawashima et al. | 435/136 |
| 5,407,957 | 4/1995 | Kyle et al. | 514/547 |
| 5,443,974 | 8/1995 | Hitz et al. | 800/264 |
| 5,492,938 | 2/1996 | Kyle et al. | 514/786 |
| 5,512,482 | 4/1996 | Voelker et al. | 435/320.1 |
| 5,545,553 | 8/1996 | Gotschlich et al. | 435/252.33 |
| 5,550,156 | 8/1996 | Kyle | 514/547 |
| 5,552,306 | 9/1996 | Thomas et al. | 435/134 |
| 5,614,393 | 3/1997 | Thomas et al. | 435/134 |
| 5,614,400 | 3/1997 | Cahoon et al. | 435/6 |

FOREIGN PATENT DOCUMENTS

| | | |
|---|---|---|
| 550162 | 7/1993 | European Pat. Off. . |
| 561569 | 9/1993 | European Pat. Off. . |
| 644263 | 3/1995 | European Pat. Off. . |
| 736598 | 10/1996 | European Pat. Off. . |
| WO 91/13972 | 9/1991 | WIPO . |
| WO 93/06712 | 4/1993 | WIPO . |
| WO 93/11245 | 6/1993 | WIPO . |
| WO 94/11516 | 5/1994 | WIPO . |
| WO 94/18337 | 8/1994 | WIPO ............ C12N 15/82 |
| WO 96/10086 | 4/1996 | WIPO . |
| WO 96/21022 | 7/1996 | WIPO . |
| WO 97/30582 | 8/1997 | WIPO ............ C12N 15/52 |

OTHER PUBLICATIONS

Ackman, "Problems in Fish Oils and Concentrates" *Canadian Inst. of Fisheries and Technology, Technical University of Nova Scotia*, pp189–204.

Bajpai and Bajpai, (1992) "Arachidonic Acid Production by Microorganisms," *Biotechnology and Applied Biochemistry*, 15:1–10.

Gurr, (Mar., 1995) "Alpha or Gamma: What's double bond Position Between Friends? 1. Gammalinolenic acid," *Lipid Technology*.

Hodgson, "Advances in Vector Systems for gene therapy," (1995) *Ex. Opin. Ther. Patents* 5(5):45.

Horrobin, "Madical Roles of Metabolites of Percursor EFA," (1995) *INFORM* 6(4):428–434.

Murata et al. "Biosynthesis of gamma–Linolenic Acid in the Cyanobacterium *Spiruline platensis*," In: *gamma–Linolenic Acid Metabolism and its roles in nutrition Medicine* (Huang and Mills, eds), pp 22–32, Access Press, Champain, IL.

Ratledge, "Single cell oils—have they a biotechnological future?" (Jul. 1995) MB Tech. 11.

Reddy and Thomas, "Expression of a cynabacterial $\Delta^6$–desaturase gene results in gamma–linolenic acid production in transgenic plants," (May, 1996) *Nature Biotechnology* 14:639–642.

Tagaki and Itabashi, "cis–5–Olefinic Unusual Fatty Acids in Seed Lipids of Gymnospermae and Their Distribution in Triacylgylycerols," (1982) *Lipids* 17(10):716–723.

Ward, "Microbial production of long–chain PUFAs," (Jun., 1995) Inform 6(6):683–688.

Wolff, "New tools to Explore lipid metabolism," (Jan., 1997) Inform 8(1):116–119.

"Closer to Mother's Milk," (Spring 1995) *The Gist* 61:8–9.

"Conifer oils offer exciting possibilities," (Jan. 1997) *Lipid Technology*.

"Exciting prospects for stearidonic acid seed oils," (Nov. 1996) *Lipid Technology*.

Primary Examiner—Elizabeth F. McElwain
Attorney, Agent, or Firm—Limbach & Limbach L.L.P.

[57] ABSTRACT

The present invention relates to compositions and methods for preparing poly-unsaturated long chain fatty acids in plants, plant parts and plant cells, such as leaves, roots, fruits and seeds. Nucleic acid sequences and constructs encoding fatty acid desaturases, including Δ5-desaturases, Δ6-desaturases and Δ12-desaturases, are used to generate transgenic plants, plant parts and cells which contain and express one or more transgenes encoding one or more desaturases. Expression of the desaturases with different substrate specificities in the plant system permit the large scale production of poly-unsaturated long chain fatty acids such as docosahexaenoic acid, eicosapentaenoic acid, α-linoleic acid, gamma-linolenic acid, arachidonic acid and the like for modification of the fatty acid profile of plants, plant parts and tissues. Manipulation of the fatty acid profiles allows for the production of commercial quantities of novel plant oils and products.

14 Claims, 21 Drawing Sheets

FIG. 3A

```
CGACACTCCT TCCTTCTTCT CACCCGTCCT AGTCCCCTTC AACCCCCCTC TTTGACAAAG   60
ACAACAAACC ATG GCT GCT GCT CCC AGT GTG AGG ACG TTT ACT CGG GCC GAG
            Met Ala Ala Ala Pro Ser Val Arg Thr Phe Thr Arg Ala Glu

GCA GTT TTG AAT GCC GAG GCT CTG AAT GAG GGC AAG AAG GAT GCC GAG GCA  120
Ala Val Leu Asn Ala Glu Ala Leu Asn Glu Gly Lys Lys Asp Ala Glu Ala

TTC CCC TTG ATG ATC ATC GAC GGA AGT ACT AAC AAG GTG TAC GAT TTC GAG  180
Phe Pro Leu Met Ile Ile Asp Gly Ser Thr Asn Lys Val Tyr Asp Phe Glu

AAG GTC CGC GAG GTC CAT CCC GGT CCC TTT GTC AGT GTG ATT CAC CTC ACG  240
Lys Val Arg Glu Val His Pro Gly Pro Phe Val Ser Val Ile His Leu Thr

CAC GTC GCT GCT GCT ACT GAC TTT TAC GTT GAT ATT GAG GCC GAG AGC GAG  300
His Val Ala Ala Ala Thr Asp Phe Tyr Val Asp Ile Glu Ala Glu Ser Glu

TGG GAG GAT CGC GAT GAT GAT TTT GCC AAC TTT GGT GAT GCG GCC GAG GTC  360
Trp Glu Asp Arg Asp Asp Asp Phe Ala Asn Phe Gly Asp Ala Ala Glu Val

CGC AAG CTG CGT ACC TTG
Arg Lys Leu Arg Thr Leu

ATC AAG AAT GAT GAC TTT GCG GCC GAG GTC CGC AAG CTG CGT ACC TTG
Ile Lys Asn Asp Asp Phe Ala Ala Glu Val Arg Lys Leu Arg Thr Leu
```

FIG. 3B

```
TTC CAG TCT CTT GGT TAC TAC GAT TCT TCC AAG GCA TAC TAC GCC TTC
Phe Gln Ser Leu Gly Tyr Tyr Asp Ser Ser Lys Ala Tyr Tyr Ala Phe
                         420*            480*

AAG GTC TCG TTC AAC CTC TGC ATC TGG GGT TTG TCG ACG GTC ATT GTG
Lys Val Ser Phe Asn Leu Cys Ile Trp Gly Leu Ser Thr Val Ile Val
                                                        540*

GCC AAG TGG GGC CAG ACC TCC ACC GCC CTC AAC GTG CTC TCG GCT GCG
Ala Lys Trp Gly Gln Thr Ser Thr Ala Leu Asn Val Leu Ser Ala Ala

CTT TTG GGT CTG TTC TGG GGA TGC GGA TGC TGG TTG GCT CAC GAC TTT
Leu Leu Gly Leu Phe Trp Gly Cys Gly Cys Trp Leu Ala His Asp Phe

TTG CAT CAC CAG GTC TTC CAG GAC CGT TTC GAT GGT GAT CTT TTC GGC
Leu His His Gln Val Phe Gln Asp Arg Phe Asp Gly Asp Leu Phe Gly
    600*

GCC TTC TTG GGA GGT GTC TGC CAG GGC TTC TCG TCC TCG TGG TGG AAG
Ala Phe Leu Gly Gly Val Cys Gln Gly Phe Ser Ser Ser Trp Trp Lys
                         660*            720*

GAC AAG CAC AAC ACT CAC CAC GCC GCC CCC AAC GTC CAC GGC GAG GAT
Asp Lys His Asn Thr His His Ala Ala Pro Asn Val His Gly Glu Asp
                                                            780*
```

| CCC | GAC | ATT | GAC | ACC | CAC | CCT | CTG | TTG | ACC | TGG | AGT | GAG | CAT | GCG | TTG |
|---|---|---|---|---|---|---|---|---|---|---|---|---|---|---|---|
| Pro | Asp | Ile | Asp | Thr | His | Pro | Leu | Leu | Thr | Trp | Ser | Glu | His | Ala | Leu |

| GAG | ATG | TTC | ATG | GTC | GAT | CCA | GTC | GAG | GAG | CTG | CTG | ACC | GAG | ATG | TCG |
|---|---|---|---|---|---|---|---|---|---|---|---|---|---|---|---|
| Glu | Met | Phe | Met | Val | Asp | Pro | Val | Glu | Glu | Leu | Leu | Thr | Glu | Met | Ser |

840*

| CGT | TTC | GCC | CGT | CTC | CTG | AAC | CAG | ACC | GAG | TAC | TTT | ATT | CTC | TCG | TCG |
|---|---|---|---|---|---|---|---|---|---|---|---|---|---|---|---|
| Arg | Phe | Ala | Arg | Leu | Leu | Asn | Gln | Thr | Glu | Tyr | Phe | Ile | Leu | Ser | Ser |

900*

| TTT | GCC | CGT | CTC | CAG | TCC | TGG | TGC | ACC | CTC | TTT | CCC | TCC | ATT | CGT | CCT |
|---|---|---|---|---|---|---|---|---|---|---|---|---|---|---|---|
| Phe | Ala | Arg | Leu | Gln | Ser | Trp | Cys | Thr | Leu | Phe | Pro | Ser | Ile | Arg | Pro |

960*

| AAC | GGT | CAG | GCC | CAC | AAG | GAT | CCC | CTC | TCG | GCG | GCG | CGT | GTG | CCC | TTG |
|---|---|---|---|---|---|---|---|---|---|---|---|---|---|---|---|
| Asn | Gly | Gln | Ala | His | Lys | Asp | Pro | Leu | Ser | Ala | Ala | Arg | Val | Pro | Leu |

| GTC | GAG | CAG | CTG | TCG | CTT | GCG | ATG | CCC | GTC | AAC | TGG | ACC | ATG | ATC | ACC |
|---|---|---|---|---|---|---|---|---|---|---|---|---|---|---|---|
| Val | Glu | Gln | Leu | Ser | Leu | Ala | Met | Pro | Val | Asn | Trp | Thr | Met | Ile | Thr |

1020*

| ATG | TTC | CTG | TTC | ATC | AAG | GAT | GCG | CTT | TCG | TAC | TAC | CTC | CTC | TAC | TTT | TTG |
|---|---|---|---|---|---|---|---|---|---|---|---|---|---|---|---|---|
| Met | Phe | Leu | Phe | Ile | Lys | Asp | Ala | Leu | Ser | Tyr | Tyr | Leu | Leu | Tyr | Phe | Leu |

1080*

| GTG | TCG | CAG | GCG | GTG | TGC | GGA | AAC | TTG | TTG | GCG | ATC | GTG | TTC | TCG | CTC |
|---|---|---|---|---|---|---|---|---|---|---|---|---|---|---|---|
| Val | Ser | Gln | Ala | Val | Cys | Gly | Asn | Leu | Leu | Ala | Ile | Val | Phe | Ser | Leu |

```
AAC  CAC  AAC  GGT  ATG  CCT  ATC  GTG  AAG  TCG  GAG  GCG  GTC  GAT  ATG
Asn  His  Asn  Gly  Met  Pro  Ile  Val  Lys  Ser  Glu  Ala  Val  Asp  Met
                                       1140*          1200*

GAT  TTC  TTC  ACG  AAG  CAG  ATC  ATC  ACG  GGT  CGT  GAT  GTC  CAC  CCG
Asp  Phe  Phe  Thr  Lys  Gln  Ile  Ile  Thr  Gly  Arg  Asp  Val  His  Pro
                                                                    1260*

CTA  TTT  GCC  AAC  TGG  TTC  ACG  GGT  GGA  TTG  AAC  TAT  CAG  ATC  GAG
Leu  Phe  Ala  Asn  Trp  Phe  Thr  Gly  Gly  Leu  Asn  Tyr  Gln  Ile  Glu

CAC  TTG  TTC  CCT  TCG  ATG  CCT  CGC  CAC  AAC  TTT  TCA  AAG  ATC  CAG
His  Leu  Phe  Pro  Ser  Met  Pro  Arg  His  Asn  Phe  Ser  Lys  Ile  Gln
         1320*

GCT  GTC  GAG  ACC  CTG  TGC  AAA  TAC  AAT  AAG  GTC  CGA  TAC  CAC  ACC
Ala  Val  Glu  Thr  Leu  Cys  Lys  Tyr  Asn  Lys  Val  Arg  Tyr  His  Thr
                                       1380*

GGT  ATG  ATC  GAG  GGA  ACT  GCA  GAG  GTC  TTT  AGC  CGT  CTG  AAC  GAG
Gly  Met  Ile  Glu  Gly  Thr  Ala  Glu  Val  Phe  Ser  Arg  Leu  Asn  Glu

TCC  AAG  GCC  TCC  AAG  ATG  TCC  AAG  GGT  AAG  GCG  CAG  ACC  GAG  GTC
Ser  Lys  Ala  Ser  Lys  Met  Ser  Lys  Gly  Lys  Ala  Gln  Thr  Glu  Val
                                                       1440*

TAAAAAAAAA  AAACAAGGAC
```

```
GTTTTTTTC GCCAGTGCCT GTGCCTGTGC CTGCTTCCCT TGTCAAGTCG AGCGTTTCTG
                                        1500
GAAAGGATCG TTCAGTGCAG TATCATCATT CTCCTTTTAC CCCCCGCTCA TATCTCATTC
                                1560
ATTTCTCTTA TTAAACAACT TGTTCCCCCC TTCACCG
```

|  | | | |
|---|---|---|---|
| Ma524   | E V R K L R T L F Q S L G Y Y D S S K A Y Y A F K V S F N L C I W G L S T V I V A K W G Q T S T L A N V L S A A L L G L | 90 |
| ATTS4723 | . . . . . . . . . . . . . . . . . . . . . . . . . . . . . . . . . . . . . V T L Y - T L A F V A A M S L G V L Y G V L A C P S V X P H Q I A A G L L G L | 38 |
| 12-5    | . . . . . . . . . . . . . . . . . . . . . . . . . . . . . . . . . . . . . . . . . . . . . . . . . . . . . . . . . . . . . G V L Y G V L A C T S V F A H Q I A A A L L G L | 24 |
| T42806  | . . . . . . . . . . . . . . . . . . . . . . G X X . . . . . . . . . . . . . . . . . . . . . . . . . . . . . . . . . . . . . . . . . . . . . . . . . . . . . | 4 |
| W28140  | . . . . . . . . . . . . . . . . . . . . . . . . . . . . . . . . . . . . . . . . . . . . . . . . . . . . . . . . . . . . . . . . . . . . . . . . . . . . . . | 1 |
| R05219  | . . . . . . . . . . . . . . . . . . . . . . . . . . . C . . . . . . . . . . . . . . . . . . . . . . . . . . . . . . . . . . . . . . . . . . . . . . . . . . | 2 |
| W53753  | . . . . . . . . . . . . . . . . . . . . . . . . . . . . . . . . . . . . . . . . . . . . . . . . . . . . . . . . . . . . . . . . . . . . . . . . . . . . . . | 1 |

|  | | | |
|---|---|---|---|
| Ma524   | F W Q Q C G W L A H D F L H H Q V F Q D R F W G D L - F G A F L G G V C - Q G F S S S W W K D K H N T H H A A P N V H G E | 119 |
| ATTS4723 | L W I Q S A Y I G X D S G H Y V I M S N K S N N X - F A Q L L S G N C L T G I . I A W W K W T H N A H H L A C N S L D Y | 97 |
| 12-5    | L W I Q S A Y I G H D S G H Y V I M S N K S Y N R - F A Q L L S G N C L T G I S I A W W K W T H N A H H L A C N S L D Y | 83 |
| T42806  | . . . . . . . . . . . . . . . . . . . . . . . . . . . . . . . . . . . . . . . . . . . . . . . . . . . . . . . . . . . . . . . . . . . . . . . . | 4 |
| W28140  | . . . . . . . . . . . . . . . . . . . . . . . . . . . . . . . . . . . . . . . . . . . . . . . . . . . . . . . . . . . . . . . . . . . . . . . . | 1 |
| R05219  | . . . . . . . . . . . . . . . . . . . . . . . . . . . . . . . . . . . . . . . . . . . . . . . . . . . . . . . . . . . . . . . . . . . . . . . . | 2 |
| W53753  | . . . . . . . . . . . . . . . . . . . . . . . . . . . . . . . . . . . . . . . . . . . . . . . . . . . . . . . . . . . . . . . . . . . . . . . . | 1 |

|  | | | |
|---|---|---|---|
| Ma524   | D P D I D T H P L L T W S E H A L E M F S D V P D E E L T R M W S - - - - - R F M V L N Q T W F Y F P I L S F A R L S W | 174 |
| ATTS4723 | G P N L Q H I P . . . . . . . . . . . . . . . . . . . . . . . . . . . . . . . . . . . . . . . . . . . . . . . . . . . . . . . . . . . . . . . . . | 105 |
| 12-5    | D P D L Q H I P V F A V S T K - - - F F S S L T S R F Y D R K L T F G P V A R F L V S Y Q H F T Y Y P V M C F G R I N L | 140 |
| T42806  | . . . . . . . . . . . . . . . . . . . . . . . . . . . . . . . . . . . . . . . . . . . . . . . . . . . . . . . . . . . . . . . . . . . . . . . . | 4 |
| W28140  | . . . . . . . . . . . . . . . . . . . . . . . . . . . . . . . . . . . . . . . . . . . . . . . . . . . . . . . . . . . . . . . . . . . . . . . . | 1 |
| R05219  | . . . . . . . . . . . . . . . . . . . . . . . . . . . . . . . . . . . . . . . . . . . . . . . . . . . . . . . . . . . . . . . . . . . . . . . . | 2 |
| W53753  | . . . . . . . . . . . . . . . . . . . . . . . . . . . . . . . . . . . . . . . . . . . . . . . . . . . . . . . . . . . . . . . . . . . . . . . . | 1 |

```
Ma524      CLQSILFVLPNGQAHKPSGARVPISLVEQLSLAM-----HWTWYLATMFLFIKDPVNMLV  229
ATTS4723                                                                    105
12-5       FIQTFLLLFSKRE--------VPDRALNFAGILV----FWTWF--PLLVSCLPNWPERF  185
T42806                         NFAGILV----FFTVF--PLLVSCLPNWPERF              29
W28140               PATEVGGLAWMIT-Y-RFFLTYVPLLGLKAFLG                       33
R05219                                    ---F-S---                           2
W53753            RHEAARGGTRLAYMLVCMQWTDL--LWAASYRFFLSYSPFYGATGTLL           48
                                       W W

Ma524      YFLVSQAVCGNLLAIVFSLNHNGMPVISKEEAVDMDFFTKQIITGRDVHPGLFANWFTGG  289
ATTS4723                                                                    105
12-5       FFVFTSFTVTALQHIIQFTLNHFAADVYV-GPPTGSDWFEKQAAGTIDISCRSYMDWFFGG  244
T42806     XFVFTGFTVTALQHIIQFTLNHFAADVYV-GPPTGSDWFEKQAAGTIDISCRSYMDWFFGG   88
W28140     LFFIVRFLESNWFVWVTQMNH---IPMHIDHDRNMDWVSTQLQATCNVHKSAFNIDWFSGH   90
R05219                         SPKSSPTRNMTPSPFIDWLWGG                       23
W53753     LFVAVRVLESHWFVWITQMNH---IPKEIGHEKHRDWASSQLAATCNVEPSLFDWFSGH    105

Ma524      LNYQIEHHLFPSMPRHNFSKIQPAVETLCKKYNVRYHTTGMIEGTAEVESRLNEVSKAAS  349
ATTS4723                                                                    105
12-5       LQFQLEHH                                                            252
T42806     LQFQLEHHLFPRLPRCHLRKVSPVGQRGFQRKXNLSX                               125
W28140     LNFQIEHHLFPTMPRHNYHXVAPLVQSLCAKHGIEYQSKPL                           131
R05219     LNYQIEHHLFPTMPRCNLNRCMKYVKEWCAENNLPYLVDDYFVGYNLNLQQLKNMAELVQ        83
W53753     LNFQIEHHLFPTMPRHNYRXVAPLVKAFCAKHGLHYEV                              143

Ma524      KMGKAQ                                                              355
ATTS4723                                                                    105
12-5                                                                         252
T42806                                                                       125
W28140                                                                       131
R05219                                                                        87
W53753     --AKAA                                                             148
```

FIG. 4B

GTCCCCTGTC GCTGTCGGCA CACCCCATCC TCCCTCGCTC CCTCTGCGTT TGTCCTTGGC  60*

CCACCGTCTC TCCTCCACCC TCCGAGACGA CTGCAACTGT AATCAGGAAC CGACAAATAC  120*

ACGATTTCTT TTTACTCAGC ACCAACTCAA AATCCTCAAC CGCAACCCTT TTTCAGG ATG  180*
                                                                Met

GCA CCT CCC AAC ACT ATC GAT GCC GGT TTG ACC CAG CGT CAT ATC AGC
Ala Pro Pro Asn Thr Ile Asp Ala Gly Leu Thr Gln Arg His Ile Ser
         240*

ACC TCG GCC CCA AAC TCG GCC AAG CCT GCC ATC CGA GAG TTC GAG CGC AAC TAC CAG
Thr Ser Ala Pro Asn Ser Ala Lys Pro Ala Ile Arg Glu Phe Glu Arg Asn Tyr Gln
                              300*

CTC CCC GAG TTC CGC GGT CTC TCC CGT GGT CTC TTC CTG GCT TGC ATC CCT GCC CAC
Leu Pro Glu Phe Arg Gly Leu Ser Arg Gly Leu Phe Leu Ala Cys Ile Pro Ala His
                                                                    360*

TGC TTT GAG CGC TGG GCG TCG CTC TTG TTC CTG GCT GCG ACC GTT CAC GTT GCC ATC GAT
Cys Phe Glu Arg Trp Ala Ser Leu Leu Phe Leu Ala Ala Thr Val His Val Ala Ile Asp
                                                                            420*

CTG ACT TGG GCG TCG CTC TTG TTG TAT TTG GCC TGG ACC CAG ATC GAC AAG
Leu Thr Trp Ala Ser Leu Leu Leu Tyr Leu Ala Trp Thr Gln Ile Asp Lys

TTT GAG AAT CCC TTG ATC CGC TAT TTG GCC TGG CCT GTT TAC TGG ATC
Phe Glu Asn Pro Leu Ile Arg Tyr Leu Ala Trp Pro Val Tyr Trp Ile

Row 1: ATG Met · CAG Gln · GGT Gly · ATT Ile (480*) · GTC Val · TGC Cys · ACC Thr · GGT Gly (540*) · GTC Val · TGG Trp · GTG Val · CTG Leu · GCT Ala · CAC His · GAG Glu · TGT Cys

Row 2: GGT Gly · CAT His · CAG Gln · TTC Phe · TCC Ser · TTC Phe · ACC Thr · TCC Ser · TGG Trp · ACC Thr · CTC Leu · AAC Asn · AAC Asn · ACA Thr · GTT Val · GGT Gly

Row 3: TGG Trp · ATC Ile · TTG Leu · ATG Met · TCG Ser · ATG Met · CTC Leu · TTG Leu · CCC Pro · TAC Tyr · CAC His (600*) · TAC Tyr · AGA Arg · ATC Ile (660*)

Row 4: TCG Ser · CAC His · TTG Leu · AAG Lys · CAC His · CAC His · AAG Lys · CAT Cat · GGC Gly · CCC Pro · ATG Met · AAG Lys · GAC Asp · CAG Gln

Row 5: GTG Val · TTT Phe · TCG Ser · CCC Pro · AAG Lys · ACC Thr · CGC Arg · ACT Thr · GGT Gly · TTG Leu · ACC Thr · CCC Pro · AAG Lys · GAG Glu

Row 6: AAC Asn · GCT Ala · GCT Ala · GTG Val · GCT Ala · GCC Ala · CAG Gln · GTT Val · GAG Glu · GAC Asp · ATG Met · TCC Ser · CAC His · CTG Leu · GAT Asp

Row 7: GAG Glu · GCT Ala · GCT Ala · CCC Pro · ATT Ile · GTG Val · ACT Thr · GAG Glu · TTC Phe · TGG Trp · ATG Met · ATG Met · ATC Ile · CAG Gln · TTC Phe · TTG Leu

Row 8: TTC Phe · GGA Gly · TGG Trp · CCC Pro · GCG Ala · TAC Tyr · CTG Leu · TAC Tyr · ATT Ile · ATG Met · AAC Asn · GCC Ala · TCT Ser (840*) · GGC Gly · CAA Gln · GAC Asp · TAC Tyr

FIG. 5C

```
900*
GGC  TGG  ACC  TTC  CAC  CAC  ACG  TAC  TCG  CCC  ATC  TTT  GAG  CCC
Gly  Trp  Thr  Phe  His  his  Thr  Tyr  Ser  Pro  Ile  Phe  Glu  Pro CGC  TTT  TTC  ATT  ATT  ATC  TCG  GAC  CTC  GGT  GTG  TTG  GCT  GCC
Arg  Phe  Phe  Ile  Ile  Ile  Ser  Asp  Leu  Gly  Val  Leu  Ala  Ala
           960*
CTC  GCC  CTG  GAC  TAT  GCC  ATG  CAG  TTG  TCG  CTC  TTG  ACC  GTC
Leu  Ala  Leu  Asp  Tyr  Ala  Met  Gln  Leu  Ser  Leu  Leu  Thr  Val
                              1020*
ACC  TAC  TAT  ATT  GTC  CCC  TAC  CTC  GTC  AAC  TTT  TGG  TTG  GTC
Thr  Tyr  Tyr  Ile  Val  Pro  Tyr  Leu  Val  Asn  Phe  Trp  Leu  Val
                                        1080*
CTG  TTC  TTC  AAT  CAG  CAG  CTC  TTT  AAG  TTT  CAT  TGG  CAT  CGC
Leu  Phe  Phe  Asn  Gln  Gln  Leu  Phe  Lys  Phe  His  Trp  His  Arg
                                                                  1140*
GAG  AAG  ACC  TTC  TTG  GAC  CCC  GAT  CTT  CCC  ACC  GTT  GAC  CGC
Glu  Lys  Thr  Phe  Leu  Asp  Pro  Asp  Leu  Pro  Thr  Val  Asp  Arg TCG  GGC  ATC  TTG  TTG  CAT  GCT  GGA  CAC  TGC  ATT  GTC  CAC  ACC
Ser  Gly  Ile  Phe  Leu  His  Ala  Gly  His  Cys  Ile  Val  His  Thr
          1200*
CAT  GCC  CAC  CAC  TTG  CAT  TTC  ATG  TTC  GGC  TAC  CAT  TAC  GCT
His  Ala  His  His  Leu  His  Phe  Met  Phe  Gly  Tyr  His  Tyr  Ala CAT  GTG  CAT  TTG  TTC  CAC  GAC  CAA  TTG  CCG  TTC  CAT  GCT  GAG
His  Val  His  Leu  Phe  His  Asp  Gln  Leu  Pro  Phe  His  Ala  Glu
```

```
                                        1260
                                          *
GAA GCT ACC TAT CAT CTC AAG AAA CTG CTG GGA GAG TAC TAT GTG TAC
Glu Ala Thr Tyr His Leu Lys Lys Leu Leu Gly Glu Tyr Tyr Val Tyr
                                                  1320
                                                    *
GAC CCA TCC CCG ATC GTC GTT GCG GTC TGG AGG TCG TTC CGT GAG TGC
Asp Pro Ser Pro Ile Val Val Ala Val Trp Arg Ser Phe Arg Glu Cys
                                                              1380
                                                                *
CGA TTC GTG GAG GAT CAG GGA GAC GTG GTC TTT TTC AAG AAG TAAAAAA
Arg Phe Val Glu Asp Gln Gly Asp Val Val Phe Phe Lys Lys
                                                            1440
                                                              *
AAAAGACAAT GGACCACACA CAACCCTTGTC TCTACAGACC TACGTATCAT GTAGCCATAC

CACTTCATAA AAGAACATGA GCTCTAGAGG CGTGTCATTC GCGCCTCC
```

FIG. 5D

```
         10          20          30          40          50          60
                                                                      *
LHHTYTNIAG  ADPDVSTSEP  DVRRIKPNQK  WFVNHINQHM  FVPFLYGLLA  FKVRIQDINI 70          80          90         100         110         120
                                                                      *
LYFVKTNDAI  RVNPISTWHT  VMFWGGKAFF  VWYRLIVPLQ  YLPLGKVLLL  FTVADMVSSY 130         140         150         160         170         180
                                                                      *
WLALTFQANY  VVEEVQWPLP  DENGIIQKDW  AAMQVETTQD  YAHDSHLWTS  ITGSLNYQXV

HHLFPH
```

```
GCTTCCTCCA GTTCATCCTC CATTTCGCCA CCTGCATTCT TTACGACCGT TAAGCAAG
                                                         60*

ATG GGA ACG GAC CAA GGA AAA ACC TTC ACC TGG GAA GAG CTG GCG GCC
met Gly Thr Asp Gln Gly Lys Thr Phe Thr Trp Glu Glu Leu Ala Ala
            120*

CAT AAC ACC AAG GAC CTA CTC TTG GCC ATC CGC GGC AGG GTG TAC
His Asn Thr Lys Asp Leu Leu Leu Ala Ile Arg Gly Arg Val Tyr

GAT GTC ACA AAG TTC TTG AGC CGC CAT CCT GGT GGA GTG GAC ACT CTC
Asp Val Thr Lys Phe Leu Ser Arg His Pro Gly Gly Val Asp Thr Leu
                            180*

CTC GGA GCT CGA GAT GTT ACT CCG GTC TTT GAG ATG TAT CAC
Leu Gly Ala Arg Asp Val Thr Pro Val Phe Glu Met Tyr His
                                        240*

TTT GGG GCT GCA GAT GCC ATT ATG AAG TAC TAT GTC ACA
Phe Gly Ala Ala Asp Ala Ile Met Lys Tyr Tyr Val Thr

GCG TCG AAT GAG CTG CCC ATC TTC CCG GAG CCA ACG GTG TTC CAC
Ala Ser Asn Glu Leu Pro Ile Phe Pro Glu Pro Thr Val Phe His
300*

CTG GTC GAG GGC TAC TTT GGT TAC ACG GTG TTC CAC
Leu Val Glu Gly Tyr Phe Gly Tyr Thr Val Phe His

AAA ACC ATC AAG AGA ACG AGA GTC GAG GGC TAC TTT ACG GAT CGG AAC ATT
Lys Thr Ile Lys Arg Thr Arg Val Glu Gly Tyr Phe Thr Asp Arg Asn Ile
            360*
```

FIG. 7B

```
GAT CCC AAG AAT AGA CCA GAG ATC TGG GGA CGA TAC GCT CTT ATC TTT
Asp Pro Lys Asn Arg Pro Glu Ile Trp Gly Arg Tyr Ala Leu Ile Phe
                            420*

GGA TCC TTG ATC GCT TCC TAC TAC GCG CAG CTC TTT GTG CCT TTC GTT
Gly Ser Leu Ile Ala Ser Tyr Tyr Ala Gln Leu Phe Val Pro Phe Val
                                                480*

GTC GAA CGC ACA TGG CTT CAG GTG GTG TTT GCA ATC ATC ATG GGA TTT
Val Glu Arg Thr Trp Leu Gln Val Val Phe Ala Ile Ile Met Gly Phe
540*

GCG TGC GCA CAA GTC GGA CTC AAC CCT CTT CAT GAT GCC TCT CAC TTT
Ala Cys Ala Gln Val Gly Leu Asn Pro Leu His Asp Ala Ser His Phe
                        600*

TCA GTG ACC CAC AAC CCC ACT GTC TGG AAG ATT CTG GGA CAA ACG CAC
Ser Val Thr His Asn Pro Thr Val Trp Lys Ile Leu Gly Gln Thr His
                                            660*

GAC TTT TTC AAC GGA GCA TCG TAC CTG GTG TGG ATG TAC CAT GCC ATG
Asp Phe Phe Asn Gly Ala Ser Tyr Leu Val Trp Met Tyr His Ala Met
                                                        720*

CTC GGC CAT CAC CCC TAC ACC AAC ATT GCT GGA GCA GAT CCC GAC GTG
Leu Gly His His Pro Tyr Thr Asn Ile Ala Gly Ala Asp Pro Asp Val
```

FIG. 7C

```
780
TCG ACG TCT GAG CCC GAT GTT CGT CTC ATC AAG CCC AAC CAA AAG TGG
Ser Thr Ser Glu Pro Asp Val Arg Leu Ile Lys Pro Asn Gln Lys Trp

TTT GTC AAC CAC ATC AAG CAC CAG ATG TTT CCT TTC TAC CTG TAC TTT
Phe Val Asn His Ile Lys His Gln Met Phe Pro Phe Tyr Leu Tyr Phe
                    840*

CTG CTG GCG TTC AAT GAC CTG CAG ATT GTG CGC AAG GTT CCT AAC ATT TTG TAC CAC GGA
Leu Leu Ala Phe Asn Asp Leu Gln Ile Val Arg Lys Val Pro Asn Ile Leu Tyr His Gly
                                    900*

GTC AAG ACC AAT GAC TGG CTG CAG TAT CTG TGG GAT AAA CCC ATC TCG ACA TGG CAC
Val Lys Thr Asn Asp Trp Leu Gln Tyr Leu Trp Asp Lys Pro Ile Ser Thr Trp His
                                            960*

ATG TTC CCC CTG CAG TAT CTG GGC AAG GCT TTC CCC TTT GTG CTG TAT CGC TTG
Met Phe Pro Leu Gln Tyr Leu Gly Lys Ala Phe Pro Phe Val Leu Tyr Arg Leu

ATT GTT CCC ATG GTG TCG TAC CTG TCT TAC TGG GCG CTG GTG GCG CTG ACC TTC
Ile Val Pro Met Val Ser Tyr Leu Ser Tyr Trp Ala Leu Val Ala Leu Thr Phe
1020
ACG GTC GCG GAC
Thr Val Ala Asp
```

```
GCG AAC CAC GTT GTT GAG GAA GTT CAG TGG CCG TTG CCT GAC GAG AAC
Ala Asn His Val Val Glu Glu Val Gln Trp Pro Leu Pro Asp Glu Asn
                1080                    1140
GGG ATC ATC CAA AAG GAC TGG GCA GCT ATG CAG GTC GAG ACT ACG CAG
Gly Ile Ile Gln Lys Asp Trp Ala Ala Met Gln Val Glu Thr Thr Gln
                                                 1200
GAT TAC GCA CAC GAT TCG CAC CTC TGG ACC AGC ATC ACT GGC AGC TTG
Asp Tyr Ala His Asp Ser His Leu Trp Thr Ser Ile Thr Gly Ser Leu

AAC TAC CAG GCT GTG CAC CAT CTG TTC CCC AAC ACC GTG TCG CAG CAC CAT
Asn Tyr Gln Ala Val His His Leu Phe Pro Asn Thr Val Ser Gln His His

TAT CCC GAT ATT CTG GCC ATC ATC AAG AAA ACC TGC AGC GAG TAC AAG
Tyr Pro Asp Ile Leu Ala Ile Ile Lys Lys Thr Cys Ser Glu Tyr Lys
                    1320

GTT CCA TAC CTT GTC AAG GAT ACG TTT TGG CAA GCA TTT GCT TCA CAT
Val Pro Tyr Leu Val Lys Asp Thr Phe Trp Gln Ala Phe Ala Ser His
                                        1380

TTG GAG CAC TTG CGT GTT CTT GGA CTC CGT CCC AAG GAA GAG TAGA
Leu Glu his Leu Arg Val Leu Gly Leu Arg Pro Lys Glu Glu
                                            1440

AGAAAAAAAG CGCCGAATGA AGTATTGCCC CCTTTTCTC CAAGAATGGC AAAAGGAGAT

CAAGTGGACA TTCTCTATGA AGA
```

```
MA29     LFPNVSQHHYPDILAIIKNTCSEYKVPYLVKDTFWQAFASHLEHLRVLGLRPKE----------E    446
MA524    LFPSMPRHNFSKIIQPAVETLCKKYNVRYHT-TGMIEGTAEVFSRLNEVSKAASKMGKAQ         457
BorD6    LFPKMPRCNLRKUSPYVIELCKKHNLPYNY-ASFSKANEMTLRTLRNTALQARDITKPLPKNLVWEALHT 446
Sy6803D6 LFPNICHIHYPQLENIIKDVCQEFGVEYKVYPTFKAAIIASNYRWLEAMGKAS                359
Sp1D6    LFPHICHIHYPKIAPILAEVCEEFGVNYAVHQTFFGALAAANYSWLKKMSINPET---------KAIEQ 365
```

FIG. 8C

METHODS AND COMPOSITIONS FOR SYNTHESIS OF LONG CHAIN POLY-UNSATURATED FATTY ACIDS IN PLANTS

CROSS-REFERENCE TO RELATED APPLICATIONS

This application is a continuation-in-part of U.S. Ser. No. 08/834,033, filed Apr. 11, 1997, and a continuation in part of U.S. Ser. No. 08/833,610, filed Apr. 11, 1997, now U.S. Pat. No. 5,972,664 which disclosures are incorporated herein by reference.

INTRODUCTION

1. Field of the Invention

This invention relates to modulating levels of enzymes and/or enzyme components capable of altering the production of long chain poly-unsaturated fatty acids (PUFAS) in a host plant. The invention is exemplified by the production of PUFAS in plants.

2. Background

Two main families of poly-unsaturated fatty acids (PUFAs) are the ω3 fatty acids, exemplified by arachidonic acid, and the ω6 fatty acids, exemplified by eicosapentaenoic acid. PUFAs are important components of the plasma membrane of the cell, where they may be found in such forms as phospholipids and triglycerides. PUFAs also serve as precursors to other molecules of importance in human beings and animals, including the prostacyclins, leukotrienes and prostaglandins. PUFAs are necessary for proper development, particularly in the developing infant brain, and for tissue formation and repair.

Four major long chain PUFAs of importance include docosahexaenoic acid (DHA) and eicosapentaenoic acid (EPA), which are primarily found in different types of fish oil, gamma-linolenic acid (GLA), which is found in the seeds of a number of plants, including evening primrose (*Oenothera biennis*), borage (*Borago officinalis*) and black currants (*Ribes nigrum*), and stearidonic acid (SDA), which is found in marine oils and plant seeds. Both GLA and another important long chain PUFA, arachidonic acid (ARA), are found in filamentous fungi. ARA can be purified from animal tissues including liver and adrenal gland. For DHA, a number of sources exist for commercial production including a variety of marine organisms, oils obtained from cold water marine fish, and egg yolk fractions. For ARA, microorganisms including the genera Mortierella, Entomophthora, Phytium and Porphyridium can be used for commercial production. Commercial sources of SDA include the genera Trichodesma and Echium. Commercial sources of GLA include evening primrose, black currants and borage. However, there are several disadvantages associated with commercial production of PUFAs from natural sources. Natural sources of PUFAs, such as animals and plants, tend to have highly heterogeneous oil compositions. The oils obtained from these sources therefore can require extensive purification to separate out one or more desired PUFAs or to produce an oil which is enriched in one or more PUFA. Natural sources also are subject to uncontrollable fluctuations in availability. Fish stocks may undergo natural variation or may be depleted by overfishing. Fish oils have unpleasant tastes and odors, which may be impossible to economically separate from the desired product, and can render such products unacceptable as food supplements. Animal oils, and particularly fish oils, can accumulate environmental pollutants. Weather and disease can cause fluctuation in yields from both fish and plant sources. Cropland available for production of alternate oil-producing crops is subject to competition from the steady expansion of human populations and the associated increased need for food production on the remaining arable land. Crops which do produce PUFAs, such as borage, have not been adapted to commercial growth and may not perform well in monoculture. Growth of such crops is thus not economically competitive where more profitable and better established crops can be grown. Large scale fermentation of organisms such as Mortierella is also expensive. Natural animal tissues contain low amounts of ARA and are difficult to process. Microorganisms such as Porphyridium and Mortierella are difficult to cultivate on a commercial scale.

Dietary supplements and pharmaceutical formulations containing PUFAs can retain the disadvantages of the PUFA source. Supplements such as fish oil capsules can contain low levels of the particular desired component and thus require large dosages. High dosages result in ingestion of high levels of undesired components, including contaminants. Care must be taken in providing fatty acid supplements, as overaddition may result in suppression of endogenous biosynthetic pathways and lead to competition with other necessary fatty acids in various lipid ω3 fractions in vivo, leading to undesirable results. For example, Eskimos having a diet high in ω3 fatty acids have an increased tendency to bleed (U.S. Pat. No. 4,874,603). Unpleasant tastes and odors of the supplements can make such regimens undesirable, and may inhibit compliance by the patient.

A number of enzymes are involved in PUFA biosynthesis. Linoleic acid (LA, 18:2 $\Delta^{9,12}$) is produced from oleic acid (18:1 $\Delta^9$) by a $\Delta$12-desaturase. GLA (18:3 $\Delta^{6,9,12}$) is produced from linoleic acid (LA, 18:2 $\Delta^{9,12}$) by a $\Delta$6-desaturase. ARA (20:4 $\Delta^{5,8,11,14}$) production from DGLA (20:3 $\Delta^{8,11,14}$) is catalyzed by a $\Delta$5-desaturase. However, animals cannot desaturate beyond the $\Delta^9$ position and therefore cannot convert oleic acid (18:1 $\Delta^9$) into linoleic acid (18:2 $\Delta^{9,12}$), Likewise, α-linolenic acid (ALA, 18:3 $\Delta^{9,12,15}$) cannot be synthesized by mammals. Other eukaryotes, including fungi and plants, have enzymes which desaturate at positions $\Delta^{12}$ and $\Delta^{15}$. The major poly-unsaturated fatty acids of animals therefore are either derived from diet and/or from desaturation and elongation of linoleic acid (18:2 $\Delta^{9,12}$) or α-linolenic acid (18:3 $\Delta^{9,12,15}$).

Poly-unsaturated fatty acids are considered to be useful for nutritional, pharmaceutical, industrial, and other purposes. An expansive supply of poly-unsaturated fatty acids from natural sources and from chemical synthesis are not sufficient for commercial needs. Therefore it is of interest to obtain genetic material involved in PUFA biosynthesis from species that naturally produce these fatty acids and to express the isolated material alone or in combination in a heterologous system which can be manipulated to allow production of commercial quantities of PUFAS.

Relevant Literature

Production of gamma-linolenic acid by a Δ6-desaturase is described in U.S. Pat. Nos. 5,552,306 and 5,614,393. Production of 8,11-eicosadienoic acid using *Mortierella alpina* is disclosed in U.S. Pat. No. 5,376,541. Production of docosahexaenoic acid by dinoflagellates is described in U.S. Pat. No. 5,407,957. Cloning of a Δ6-desaturase from borage is described in PCT publication WO 96/21022. Cloning of Δ9-desaturases is described in the published patent applications PCT WO 91/13972, EP 0 550 162 A1, EP 0 561 569 A2, EP 0 644 263 A2, and EP 0 736 598 A1, and in U.S. Pat. No. 5,057,419. Cloning of Δ12-desaturases from various organisms is described in PCT publication WO 94/11516 and U.S. Pat. No. 5,443,974. Cloning of Δ15-desaturases from various organisms is described in PCT publication WO 93/11245. A Δ6 palmitoyl-acyl carrier protein desaturase from *Thumbergia alata* and its expression in *E. coli* is described in U.S. Pat. No. 5,614,400. Expression of a soybean stearyl-ACP desaturase in transgenic soybean embryos using a 35S promoter is disclosed in U.S. Pat. No. 5,443,974.

SUMMARY OF THE INVENTION

Novel compositions and methods are provided for preparation of poly-unsaturated long chain fatty acids and desaturases in plants and plant cells. The methods involve growing a host plant cell of interest transformed with an expression cassette functional in a host plant cell, the expression cassette comprising a transcriptional and translational initiation regulatory region, joined in reading frame 5' to a DNA sequence encoding a desaturase polypeptide capable of modulating the production of PUFAs. Expression of the desaturase polypeptide provides for an alteration in the PUFA profile of host plant cells as a result of altered concentrations of enzymes involved in PUFA biosynthesis. Of particular interest is the selective control of PUFA production in plant tissues and/or plant parts such as leaves, roots, fruits and seeds. The invention finds use for example in the large scale production of DHA, EPA, ALA, and GLA and for modification of the fatty acid profile of edible plant tissues and/or plant parts.

BRIEF DESCRIPTION OF THE DRAWINGS

FIGS. 3A–E shows the DNA sequence (SEQ ID NO:1) of the *Mortierella alpina* $\Delta 6$ desaturase and the deduced amino acid sequence (SEQ ID NO:2).

FIG. 4 shows an alignment of the *Mortierella alpina* $\Delta 6$ desaturase partial amino acid sequence (Ma524, SEQ ID NO:7) with other $\Delta 6$ desaturases and related sequences (SEQ ID NOS:8, 9, 10, 11, 12 and 13).

FIGS. 5A–D shows the DNA sequence of the *Mortierella alpina* $\Delta 12$ desaturase (SEQ ID NO:3) and the deduced amino acid sequence (SEQ ID NO:4).

FIG. 6 shows the deduced amino acid sequence (SEQ ID NO:14) of the PCR fragment (see Example 1).

FIGS. 7A–D shows the DNA sequence of the *Mortierella alpina* $\Delta 5$ desaturase (SEQ ID NO:5) and the deduced amino acid sequence (SEQ ID NO:6).

BRIEF DESCRIPTION OF THE SEQUENCE LISTINGS

Figure 1:
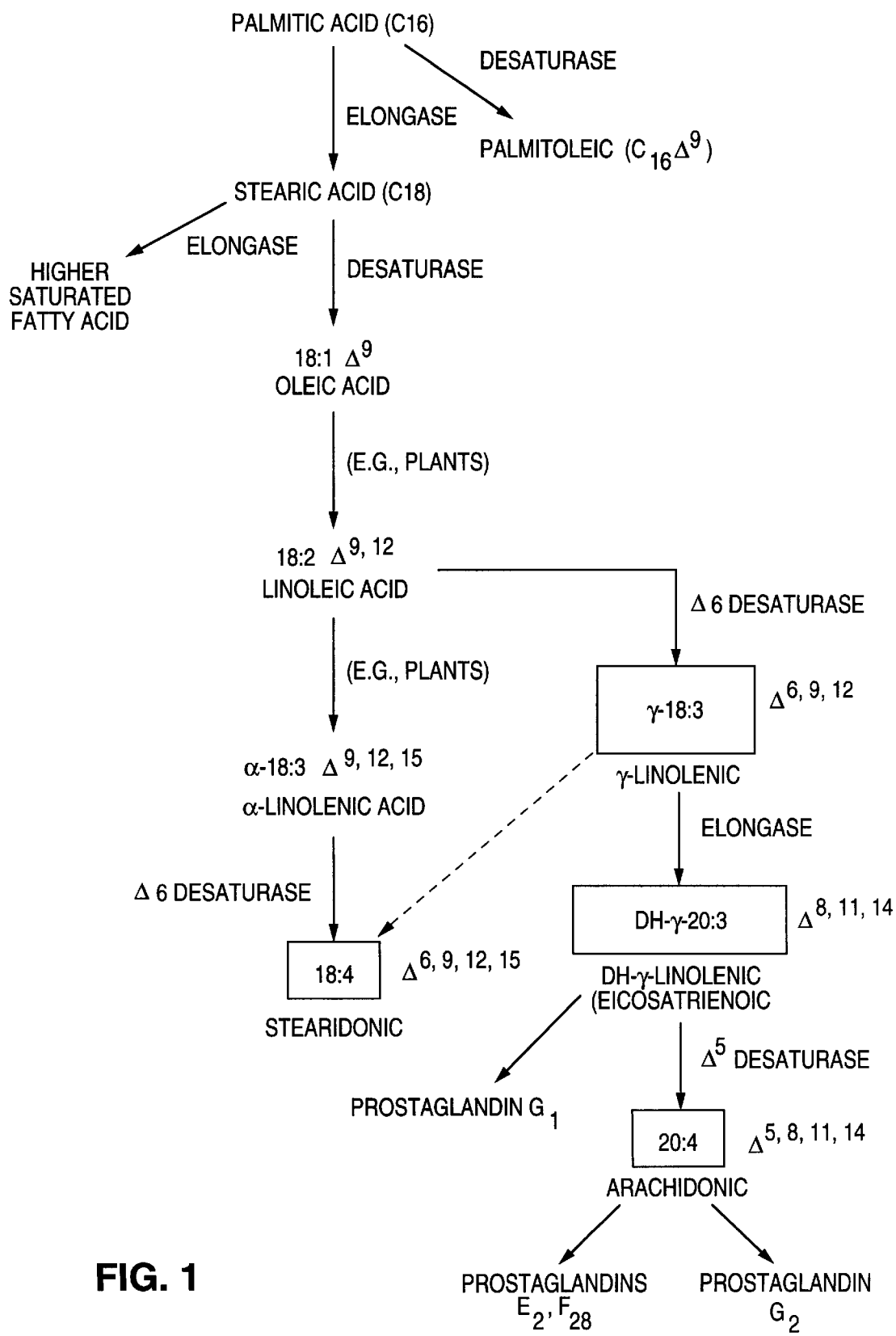
FIG. 1 shows possible pathways for the synthesis of arachidonic acid (20:4 $\Delta^{5,8,11,14}$) and stearidonic acid (18:4 $\Delta^{6,9,12,15}$) from palmitic acid ($C_{16}$) from a variety of organisms, including algae, Mortierella and humans. These PUFAs can serve as precursors to other molecules important for humans and other animals, including prostacyclins, leukotrienes, and prostaglandins, some of which are shown.

SEQ ID NO:1 shows the DNA sequence of the *Mortierella alpina* $\Delta 6$ desaturase.

SEQ ID NO:2 shows the amino acid sequence of the *Mortierella alpina* $\Delta 6$ desaturase.

SEQ ID NO:3 shows the DNA sequence of the *Mortierella alpina* $\Delta 12$ desaturase.

SEQ ID NO:4 shows the amino acid sequence of the *Mortierella alpina* $\Delta 12$ desaturase.

SEQ ID NO:5 shows the DNA sequence of the *Mortierella alpina* $\Delta 12$ desaturase.

SEQ ID NO:6 shows the amino acid sequence *Mortierella alpina* $\Delta 5$ desaturase.

DESCRIPTION OF THE PREFERRED EMBODIMENTS

In accordance with the subject invention, novel DNA sequences, DNA constructs, methods and compositions are provided which permit modification of the poly-unsaturated long chain fatty acid content of plant cells. Plant cells are transformed with an expression cassette comprising a DNA encoding a polypeptide capable of increasing the amount of one or more PUFA in a plant cell. Desirably, integration constructs may be prepared which provide for integration of the expression cassette into the genome of a host cell. Host cells are manipulated to express a sense or antisense DNA encoding a polypeptide(s) that has desaturase activity. By "desaturase" is intended a polypeptide which can desaturate one or more fatty acids to produce a mono- or poly-unsaturated fatty acid or precursor thereof of interest. By "polypeptide" is meant any chain of amino acids, regardless of length or post-translational modification, for example, glycosylation or phosphorylation. The substrate(s) for the expressed enzyme may be produced by the host cell or may be exogenously supplied.

To achieve expression in a host cell, the transformed DNA is operably associated with transcriptional and translational initiation and termination regulatory regions that are functional in the host cell. Constructs comprising the gene to be expressed can provide for integration into the genome of the host cell or can autonomously replicate in the host cell. For production of linoleic acid (LA), the expression cassettes generally used include a cassette which provides for $\Delta 12$ desaturase activity, particularly in a host cell which produces or can take up oleic acid. For production of ALA, the expression cassettes generally used include a cassette which provides for $\Delta 15$ or $\omega 3$ desaturase activity, particularly in a host cell which produces or can take up LA. For production of GLA or SDA, the expression cassettes generally used include a cassette which provides for $\Delta 6$ desaturase activity, particularly in a host cell which produces or can take up LA or ALA, respectively. Production of $\omega 6$-type unsaturated fatty acids, such as LA or GLA, is favored in a plant capable of producing ALA by inhibiting the activity of a $\Delta 15$ or $\omega 3$ type desaturase; this is accomplished by providing an expression cassette for an antisense $\Delta 15$ or $\omega 3$ transcript, or by disrupting a $\Delta 15$ or $\omega 3$ desaturase gene. Similarly, production of LA or ALA is favored in a plant having $\Delta 6$ desaturase activity by providing an expression cassette for an antisense $\Delta 6$ transcript, or by disrupting a $\Delta 6$ desaturase gene. Production of oleic acid likewise is favored in a plant having $\Delta 12$ desaturase activity by providing an expression cassette for an antisense $\Delta 12$ transcript, or by disrupting a $\Delta 12$ desaturase gene. For production of ARA, the expression cassette generally used provides for $\Delta 5$ desaturase activity, particularly in a host cell which produces or can take up DGLA. Production of $\omega 6$-type unsaturated fatty acids, such as ARA, is favored in a plant capable of producing ALA by inhibiting the activity of a $\Delta 15$ or $\omega 3$ type desaturase; this is accomplished by providing an expression cassette for an antisense $\Delta 15$ or $\omega 3$ transcript, or by disrupting a $\Delta 15$ or $\omega 3$ desaturase gene.

Transgenic plant production of PUFAs offers several advantages over purification from natural sources such as fish or plants. Production of fatty acids from recombinant plants provides the ability to alter the naturally occurring plant fatty acid profile by providing new synthetic pathways in the host or by suppressing undesired pathways, thereby increasing levels of desired PUFAs, or conjugated forms thereof, and decreasing levels of undesired PUFAs. Production of fatty acids in transgenic plants also offers the advantage that expression of desaturase genes in particular tissues and/or plant parts means that greatly increased levels of desired PUFAs in those tissues and/or parts can be achieved, making recovery from those tissues more economical. For example, the desired PUFAs can be expressed in seed; methods of isolating seed oils are well established. In addition to providing a source for purification of desired PUFAs, seed oil components can be manipulated through expression of desaturase genes, either alone or in combination with other genes such as elongases, to provide seed oils having a particular PUFA profile in concentrated form. The concentrated seed oils then can be added to animal milks and/or synsythetic or semisythetic milks to serve as infant formulas where human nursing is impossible or undesired, or in cases of malnourishment or disease in both adults and infants.

Figure 2:
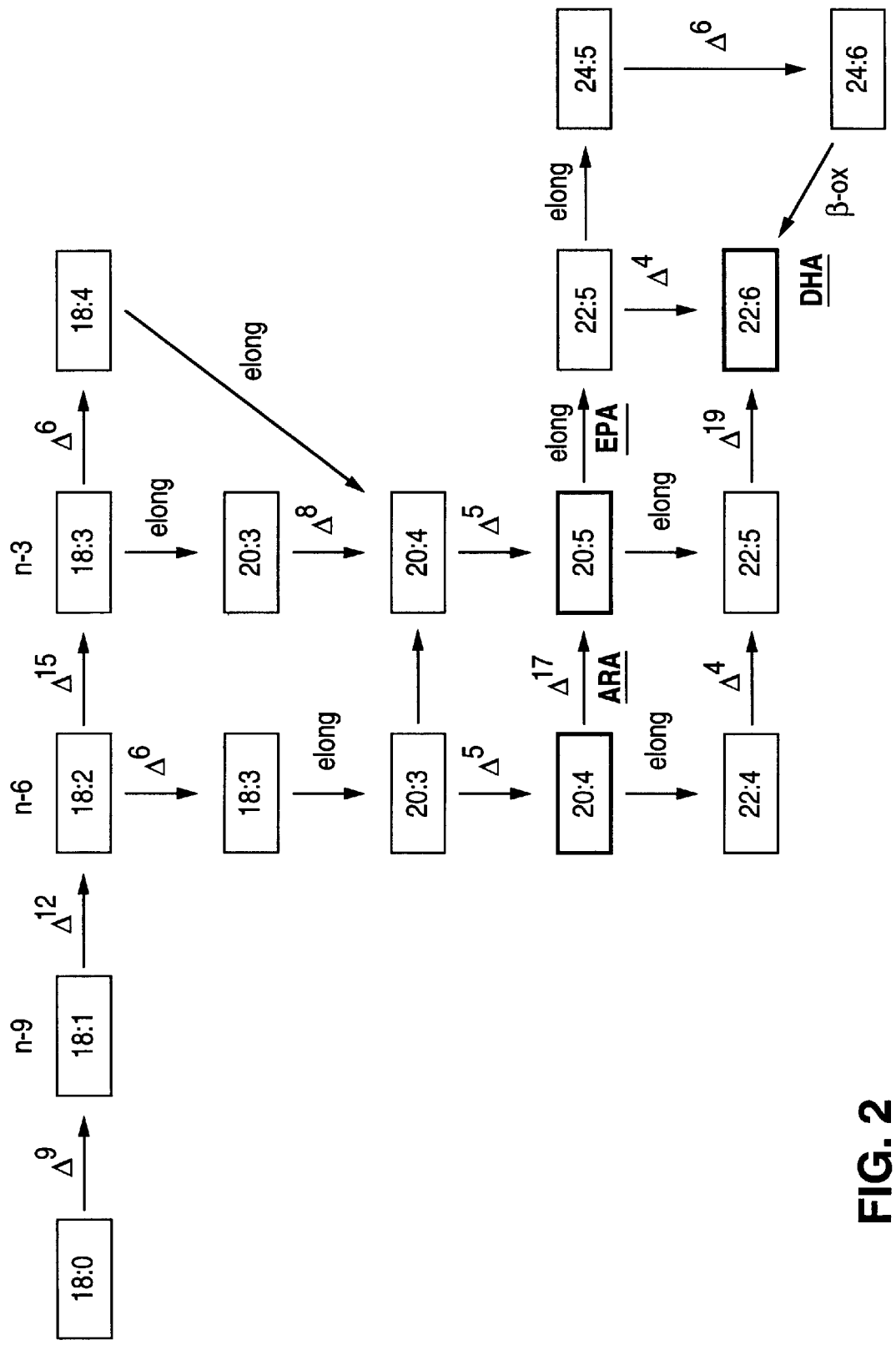
FIG. 2 shows possible pathways for production of PUFAs in addition to ARA, including EPA and DHA, again compiled from a variety of organisms.

For production of PUFAs, depending upon the host cell, the availability of substrate, and the desired end product(s), several polypeptides, particularly desaturases, are of interest including those polypeptides which catalyze the conversion of stearic acid to oleic acid, LA to GLA, of ALA to SDA, of oleic acid to LA, or of LA to ALA, which includes enzymes which desaturate at the Δ6, Δ9, Δ12, Δ15 or ω3 positions. Considerations for choosing a specific polypeptide having desaturase activity include the pH optimum of the polypeptide, whether the polypeptide is a rate limiting enzyme or a component thereof, whether the desaturase used is essential for synthesis of a desired poly-unsaturated fatty acid, and/or co-factors required by the polypeptide. The expressed polypeptide preferably has parameters compatible with the biochemical environment of its location in the host cell. For example, the polypeptide may have to compete for substrate with other enzymes in the host cell. Analyses of the Km and specific activity of the polypeptide in question therefore are considered in determining the suitability of a given polypeptide for modifying PUFA production in a given host cell. The polypeptide used in a particular situation therefore is one which can function under the conditions present in the intended host cell but otherwise can be any polypeptide having desaturase activity which has the desired characteristic of being capable of modifying the relative production of a desired PUFA. A scheme for the synthesis of arachidonic acid (20:4 $\Delta^{5,8,11,14}$) from palmitic acid ($C_{16}$) is shown in Figure 1. A key enzyme in this pathway is a Δ5-desaturase which converts DH-γ-linolenic acid (DGLA, eicosatrienoic acid) to ARA. Conversion of α-linolenic acid (ALA) to stearidonic acid by a Δ6-desaturase is also shown. Production of PUFAs in addition to ARA, including EPA and DHA is shown in FIG. 2. A key enzyme in the synthesis of arachidonic acid (20:4 $\Delta^{5,8,11,14}$) from stearic acid ($C_{18}$) is a Δ6-desaturase which converts the linoleic acid into γ-linolenic acid. Conversion of α-linolenic acid (ALA) to stearidonic acid by a Δ6-desaturase also is shown. For production of ARA, the DNA sequence used encodes a polypeptide having Δ5 desaturase activity. In particular instances, this can be coupled with an expression cassette which provides for production of a polypeptide having Δ6 desaturase activity and, optionally, a transcription cassette providing for production of antisense sequences to a Δ15 transcription product. The choice of combination of cassettes used depends in part on the PUFA profile of the host cell. Where the host cell Δ5-desaturase activity is limiting, overexpression of Δ5 desaturase alone generally will be sufficient to provide for enhanced ARA production.

As sources of polypeptides having desaturase activity and oligonucleotides encoding such polypeptides are organisms which produce a desired poly-unsaturated fatty acid. As an example, microorganisms having an ability to produce ARA can be used as a source of Δ5-desaturase genes; microorganisms which GLA or SDA can be used as a source of Δ6-desaturase and/or Δ12-desaturase genes. Such microorganisms include, for example, those belonging to the genera Mortierella, Conidiobolus, Pythium, Phytophathora, Penicillium, Porphyridium, Coidosporium, Mucor, Fusarium, Aspergillus, Rhodotorula, and Entomophthora. Within the genus Porphyridium, of particular interest is *Porphyridium cruentum*. Within the genus Mortierella, of particular interest are *Mortierella elongata, Mortierella exigua, Mortierella hygrophila, Mortierella ramanniana*, var. *angulispora*, and *Mortierella alpina*. Within the genus Mucor, of particular interest are *Mucor circinelloides* and *Mucor javanicus*.

DNAs encoding desired desaturases can be identified in a variety of ways. As an example, a source of the desired desaturase, for example genomic or cDNA libraries from Mortierella, is screened with detectable enzymatically- or chemically-synthesized probes, which can be made from DNA, RNA, or non-naturally occurring nucleotides, or mixtures thereof. Probes may be enzymatically synthesized from DNAs of known desaturases for normal or reduced-stringency hybridization methods. Oligonucleotide probes also can be used to screen sources and can be based on sequences of known desaturases, including sequences conserved among known desaturases, or on peptide sequences obtained from the desired purified protein. Oligonucleotide probes based on amino acid sequences can be degenerate to encompass the degeneracy of the genetic code, or can be biased in favor of the preferred codons of the source organism. Oligonucleotides also can be used as primers for PCR from reverse transcribed mRNA from a known or suspected source; the PCR product can be the full length cDNA or can be used to generate a probe to obtain the desired full length cDNA. Alternatively, a desired protein can be entirely sequenced and total synthesis of a DNA encoding that polypeptide performed.

Once the desired genomic or cDNA has been isolated, it can be sequenced by known methods. It is recognized in the art that such methods are subject to errors, such that multiple sequencing of the same region is routine and is still expected to lead to measurable rates of mistakes in the resulting deduced sequence, particularly in regions having repeated domains, extensive secondary structure, or unusual base compositions, such as regions with high GC base content. When discrepancies arise, resequencing can be done and can employ special methods. Special methods can include altering sequencing conditions by using: different temperatures; different enzymes; proteins which alter the ability of oligonucleotides to form higher order structures; altered nucleotides such as ITP or methylated dGTP; different gel compositions, for example adding formamide; different primers or primers located at different distances from the problem region; or different templates such as single stranded DNAs. Sequencing of mRNA can also be employed.

For the most part, some or all of the coding sequence for the polypeptide having desaturase activity is from a natural source. In some situations, however, it is desirable to modify all or a portion of the codons, for example, to enhance expression, by employing host preferred codons. Host preferred codons can be determined from the codons of highest frequency in the proteins expressed in the largest amount in a particular host species of interest. Thus, the coding sequence for a polypeptide having desaturase activity can be synthesized in whole or in part. All or portions of the DNA also can be synthesized to remove any destabilizing sequences or regions of secondary structure which would be present in the transcribed mRNA. All or portions of the DNA also can be synthesized to alter the base composition to one more preferable in the desired host cell. Methods for synthesizing sequences and bringing sequences together are well established in the literature. In vitro mutagenesis and selection, site-directed mutagenesis, or other means can be employed to obtain mutations of naturally occurring desaturase genes to produce a polypeptide having desaturase activity in vivo with more desirable physical and kinetic parameters for function in the host cell, such as a longer half-life or a higher rate of production of a desired polyunsaturated fatty acid.

Desirable cDNAs have less than 60% A+T composition, preferably less than 50% A+T composition. On a localized scale of a sliding window of 20 base pairs, it is preferable that there are no localized regions of the cDNA with greater than 75% A+T composition; with a window of 60 base pairs, it is preferable that there are no localized regions of the cDNA with greater than 60%, more preferably no localized regions with greater than 55% A+T composition.

Of particular interest are the *Mortierella alpina* Δ5-desaturase, Δ6-desaturase and Δ12-desaturase. The Δ5-desaturase has 446 amino acids; the amino acid sequence is shown in FIG. 6. The gene encoding the *Mortierella alpina* Δ5-desaturase can be expressed in transgenic microorganisms to effect greater synthesis of ARA from DGLA. Other DNAs which are substantially identical in sequence to the *Mortierella alpina* Δ5-desaturase DNA, or which encode polypeptides which are substantially identical in sequence to the *Mortierella alpina* Δ5-desaturase polypeptide, also can be used. The *Mortierella alpina* Δ6-desaturase, has 457 amino acids and a predicted molecular weight of 51.8 kD; the amino acid sequence is shown in FIG. 2. The gene encoding the *Mortierella alpina* Δ6-desaturase can be expressed in transgenic plants or animals to effect greater synthesis of GLA from linoleic acid or of stearidonic acid (SDA) from ALA. Other DNAs which are substantially identical in sequence to the *Mortierella alpina* Δ6-desaturase DNA, or which encode polypeptides which are substantially identical in sequence to the *Mortierella alpina* Δ6-desaturase polypeptide, also can be used.

The *Mortierella alpina* Δ12-desaturase has the amino acid sequence shown in FIG. 4. The gene encoding the *Mortierella alpina* Δ12-desaturase can be expressed in transgenic plants to effect greater synthesis of LA from oleic acid. Other DNAs which are substantially identical to the *Mortierella alpina* Δ12-desaturase DNA, or which encode polypeptides which are substantially identical to the *Mortierella alpina* Δ12-desaturase polypeptide, also can be used. By substantially identical in sequence is intended an amino acid sequence or nucleic acid sequence exhibiting in order of increasing preference at least 60%, 80%, 90% or 95% homology to the *Mortierella alpina* Δ5-desaturase amino acid sequence or nucleic acid sequence encoding the amino acid sequence. For polypeptides, the length of comparison sequences generally is at least 16 amino acids, preferably at least 20 amino acids, or most preferably 35 amino acids. For nucleic acids, the length of comparison sequences generally is at least 50 nucleotides, preferably at least 60 nucleotides, and more preferably at least 75 nucleotides, and most preferably, 110 nucleotides. Homology typically is measured using sequence analysis software, for example, the Sequence Analysis software package of the Genetics Computer Group, University of Wisconsin Biotechnology Center, 1710 University Avenue, Madison, Wis. 53705, MEGAlign (DNAStar, Inc., 1228 S. Park St., Madison, Wis. 53715), and MacVector (Oxford Molecular Group, 2105 S. Bascom Avenue, Suite 200, Campbell, Calif. 95008). Such software matches similar sequences by assigning degrees of homology to various substitutions, deletions, and other modifications. Conservative substitutions typically include substitutions within the following groups: glycine and alanine; valine, isoleucine and leucine; aspartic acid, glutamic acid, asparagine, and glutamine; serine and threonine; lysine and arginine; and phenylalanine and tyrosine. Substitutions may also be made on the basis of conserved hydrophobicity or hydrophilicity (Kyte and Doolittle, *J. Mol. Biol.* 157:105–132, 1982), or on the basis of the ability to assume similar polypeptide secondary structure (Chou and Fasman, *Adv. Enzymol.* 47:45–148, 1978).

Encompassed by the present invention are related desaturases from the same or other organisms. Such related desaturases include variants of the disclosed Δ5-, Δ6- and Δ12-desaturases that occur naturally within the same or different species of Mortierella, as well as homologues of the disclosed Δ5-desaturase from other species and evolutionarily related protein having desaturase activity. Also included are desaturases which, although not substantially identical to the *Mortierella alpina* Δ5-desaturase, desaturate a fatty acid molecule at carbon 4, 5, or 11 respectively, from the carboxyl end of a fatty acid molecule. Related desaturases can be identified by their ability to function substantially the same as the disclosed desaturases; that is, are still able to effectively convert DGLA to ARA, LA to GLA, ALA to SDA or oleic acid to LA. Related desaturases also can be identified by screening sequence databases for sequences homologous to the disclosed desaturase, by hybridization of a probe based on the disclosed desaturase to a library constructed from the source organism, or by RT-PCR using mRNA from the source organism and primers based on the disclosed desaturase.

The regions of a desaturase polypeptide important for desaturase activity can be determined through routine mutagenesis, expression of the resulting mutant polypeptides and determination of their activities. Mutants may include deletions, insertions and point mutations, or combinations thereof. A typical functional analysis begins with deletion mutagenesis to determine the N- and C-terminal limits of the protein necessary for function, and then internal deletions, insertions or point mutants are made to further determine regions necessary for function. Other techniques such as cassette mutagenesis or total synthesis also can be used. Deletion mutagenesis is accomplished, for example, by using exonucleases to sequentially remove the 5' or 3' coding regions. Kits are available for such techniques. After deletion, the coding region is completed by ligating oligonucleotides containing start or stop codons to the deleted coding region after 5' or 3' deletion, respectively. Alternatively, oligonucleotides encoding start or stop codons are inserted into the coding region by a variety of methods including site-directed mutagenesis, mutagenic PCR or by ligation onto DNA digested at existing restriction sites. Internal deletions can similarly be made through a variety of methods including the use of existing restriction sites in the DNA, by use of mutagenic primers via site directed mutagenesis or mutagenic PCR. Insertions are made through methods such as linker-scanning mutagenesis, site-directed mutagenesis or mutagenic PCR. Point mutations are made through techniques such as site-directed mutagenesis or mutagenic PCR.

Chemical mutagenesis can also be used for identifying regions of a desaturase polypeptide important for activity. A mutated construct is expressed, and the ability of the resulting altered protein to function as a desaturase is assayed. Such structure-function analysis can determine which regions may be deleted, which regions tolerate insertions, and which point mutations allow the mutant protein to function in substantially the same way as the native desaturase. All such mutant proteins and nucleotide sequences encoding them are within the scope of the present invention.

Once the DNA encoding a desaturase polypeptide has been obtained, it is placed in a vector capable of replication in a host cell, or is propagated in vitro by means of techniques such as PCR or long PCR. Replicating vectors can include plasmids, phage, viruses, cosmids and the like. Desirable vectors include those useful for mutagenesis of the gene of interest or for expression of the gene of interest in host cells. The technique of long PCR has made in vitro propagation of large constructs possible, so that modifications to the gene of interest, such as mutagenesis or addition of expression signals, and propagation of the resulting constructs can occur entirely in vitro without the use of a replicating vector or a host cell.

For expression of a desaturase polypeptide, functional transcriptional and translational initiation and termination regions are operably linked to the DNA encoding the desaturase polypeptide. Transcriptional and translational initiation and termination regions are derived from a variety of nonexclusive sources, including the DNA to be expressed, genes known or suspected to be capable of expression in the desired system, expression vectors, chemical synthesis, or from an endogenous locus in a host cell. Expression in a plant tissue and/or plant part presents certain efficiencies, particularly where the tissue or part is one which is easily harvested, such as seed, leaves, fruits, flowers, roots, etc. Expression can be targeted to that location within the plant by using specific regulatory sequences, such as those of U.S. Pat. Nos. 5,463,174, 4,943,674, 5,106,739, 5,175,095, 5,420,034, 5,188,958, and 5,589,379. Alternatively, the expressed protein can be an enzyme which produces a product which may be incorporated, either directly or upon further modifications, into a fluid fraction from the host plant. In the present case, expression of desaturase genes, or antisense desaturase transcripts, can alter the levels of specific PUFAs, or derivatives thereof, found in plant parts and/or plant tissues. The $\Delta 5$-desaturase polypeptide coding region is expressed either by itself or with other genes, in order to produce tissues and/or plant parts containing higher proportions of desired PUFAs or in which the PUFA composition more closely resembles that of human breast milk (Prieto et al., PCT publication WO 95/24494). The termination region can be derived from the 3' region of the gene from which the initiation region was obtained or from a different gene. A large number of termination regions are known to and have been found to be satisfactory in a variety of hosts from the same and different genera and species. The termination region usually is selected more as a matter of convenience rather than because of any particular property.

The choice of a host cell is influenced in part by the desired PUFA profile of the transgenic cell, and the native profile of the host cell. As an example, for production of linoleic acid from oleic acid, the DNA sequence used encodes a polypeptide having $\Delta 12$ desaturase activity, and for production of GLA from linoleic acid, the DNA sequence used encodes a polypeptide having $\Delta 6$ desaturase activity. Use of a host cell which expresses $\Delta 12$ desaturase activity and lacks or is depleted in $\Delta 15$ desaturase activity, can be used with an expression cassette which provides for overexpression of $\Delta 6$ desaturase alone generally is sufficient to provide for enhanced GLA production in the transgenic cell. Where the host cell expresses $\Delta 9$ desaturase activity, expression of both a $\Delta 12$- and a $\Delta 6$-desaturase can provide for enhanced GLA production. In particular instances where expression of $\Delta 6$ desaturase activity is coupled with expression of $\Delta 12$ desaturase activity, it is desirable that the host cell naturally have, or be mutated to have, low $\Delta 15$ desaturase activity. Alternatively, a host cell for $\Delta 6$ desaturase expression may have, or be mutated to have, high $\Delta 12$ desaturase activity.

Expression in a host cell can be accomplished in a transient or stable fashion. Transient expression can occur from introduced constructs which contain expression signals functional in the host cell, but which constructs do not replicate and rarely integrate in the host cell, or where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct that can integrate into the host genome or that autonomously replicates in the host cell. Stable expression of the gene of interest can be selected for through the use of a selectable marker located on or transfected with the expression construct, followed by selection for cells expressing the marker. When stable expression results from integration, integration of constructs can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

When increased expression of the desaturase polypeptide in the source plant is desired, several methods can be employed. Additional genes encoding the desaturase polypeptide can be introduced into the host organism. Expression from the native desaturase locus also can be increased through homologous recombination, for example by inserting a stronger promoter into the host genome to cause increased expression, by removing destabilizing sequences from either the mRNA or the encoded protein by deleting that information from the host genome, or by adding stabilizing sequences to the mRNA (see U.S. Pat. Nos. 4,910,141 and 5,500,365.)

When it is desirable to express more than one different gene, appropriate regulatory regions and expression methods, introduced genes can be propagated in the host cell through use of replicating vectors or by integration into the host genome. Where two or more genes are expressed from separate replicating vectors, it is desirable that each vector has a different means of replication. Each introduced construct, whether integrated or not, should have a different means of selection and should lack homology to the other constructs to maintain stable expression and prevent reassortment of elements among constructs. Judicious choices of regulatory regions, selection means and method of propagation of the introduced construct can be experimentally determined so that all introduced genes are expressed at the necessary levels to provide for synthesis of the desired products.

Constructs comprising the gene of interest may be introduced into a host cell by standard techniques. These techniques include transfection, infection, bolistic impact, electroporation, microinjection, scraping, or any other method which introduces the gene of interest into the host cell (see U.S. Pat. Nos. 4,743,548, 4,795,855, 5,068,193, 5,188,958, 5,463,174, 5,565,346 and 5,565,347). For convenience, a host cell which has been manipulated by any method to take up a DNA sequence or construct will be referred to as "transformed" or "recombinant" herein. The subject host will have at least have one copy of the expression construct and may have two or more, depending upon whether the gene is integrated into the genome, amplified, or is present on an extrachromosomal element having multiple copy numbers.

The transformed host cell can be identified by selection for a marker contained on the introduced construct. Alternatively, a separate marker construct may be introduced with the desired construct, as many transformation techniques introduce many DNA molecules into host cells. Typically, transformed hosts are selected for their ability to grow on selective media. Selective media may incorporate an antibiotic or lack a factor necessary for growth of the untransformed host, such as a nutrient or growth factor. An introduced marker gene therefor may confer antibiotic resistance, or encode an essential growth factor or enzyme, and permit growth on selective media when expressed in the transformed host cell. Desirably, resistance to kanamycin and the amino glycoside G418 are of interest (see U.S. Pat. No. 5,034,322). Selection of a transformed host can also occur when the expressed marker protein can be detected, either directly or indirectly. The marker protein may be expressed alone or as a fusion to another protein. The marker protein can be detected by its enzymatic activity; for example β galactosidase can convert the substrate X-gal to a colored product, and luciferase can convert luciferin to a light-emitting product. The marker protein can be detected by its light-producing or modifying characteristics; for example, the green fluorescent protein of *Aequorea victoria* fluoresces when illuminated with blue light. Antibodies can be used to detect the marker protein or a molecular tag on, for example, a protein of interest. Cells expressing the marker protein or tag can be selected, for example, visually, or by techniques such as FACS or panning using antibodies.

The PUFAs produced using the subject methods and compositions may be found in the host plant tissue and/or plant part as free fatty acids or in conjugated forms such as acylglycerols, phospholipids, sulfolipids or glycolipids, and may be extracted from the host cell through a variety of means well-known in the art. Such means may include extraction with organic solvents, sonication, supercritical fluid extraction using for example carbon dioxide, and physical means such as presses, or combinations thereof. Of particular interest is extraction with methanol and chloroform. Where desirable, the aqueous layer can be acidified to protonate negatively charged moieties and thereby increase partitioning of desired products into the organic layer. After extraction, the organic solvents can be removed by evaporation under a stream of nitrogen. When isolated in conjugated forms, the products are enzymatically or chemically cleaved to release the free fatty acid or a less complex conjugate of interest, and are then subjected to further manipulations to produce a desired end product. Desirably, conjugated forms of fatty acids are cleaved with potassium hydroxide.

If further purification is necessary, standard methods can be employed. Such methods include extraction, treatment with urea, fractional crystallization, HPLC, fractional distillation, silica gel chromatography, high speed centrifugation or distillation, or combinations of these techniques. Protection of reactive groups, such as the acid or alkenyl groups, may be done at any step through known techniques, for example alkylation or iodination. Methods used include methylation of the fatty acids to produce methyl esters. Similarly, protecting groups may be removed at any step. Desirably, purification of fractions containing ARA, DHA and EPA is accomplished by treatment with urea and/or fractional distillation.

The uses of the subject invention are several. Probes based on the DNAs of the present invention may find use in methods for isolating related molecules or in methods to detect organisms expressing desaturases. When used as probes, the DNAs or oligonucleotides need to be detectable. This is usually accomplished by attaching a label either at an internal site, for example via incorporation of a modified residue, or at the 5' or 3' terminus. Such labels can be directly detectable, can bind to a secondary molecule that is detectably labeled, or can bind to an unlabelled secondary molecule and a detectably labeled tertiary molecule; this process can be extended as long as is practical to achieve a satisfactorily detectable signal without unacceptable levels of background signal. Secondary, tertiary, or bridging systems can include use of antibodies directed against any other molecule, including labels or other antibodies, or can involve any molecules which bind to each other, for example a biotin-streptavidin/avidin system. Detectable labels typically include radioactive isotopes, molecules which chemically or enzymatically produce or alter light, enzymes which produce detectable reaction products, magnetic molecules, fluorescent molecules or molecules whose fluorescence or light-emitting characteristics change upon binding. Examples of labelling methods can be found in U.S. Pat. No. 5,011,770. Alternatively, the binding of target molecules can be directly detected by measuring the change in heat of solution on binding of probe to target via isothermal titration calorimetry, or by coating the probe or target on a surface and detecting the change in scattering of light from the surface produced by binding of target or probe, respectively, as may be done with the BIAcore system.

PUFAs produced by recombinant means find applications in a wide variety of areas. Supplementation of humans or animals with PUFAs in various forms can result in increased levels not only of the added PUFAs, but of their metabolic progeny as well. For example, where the inherent Δ6-desaturase pathway is dysfunctional in an individual, treatment with GLA can result not only in increased levels of GLA, but also of downstream products such as ARA and prostaglandins (see FIG. 1). Complex regulatory mechanisms can make it desirable to combine various PUFAs, or to add different conjugates of PUFAs, in order to prevent, control or overcome such mechanisms to achieve the desired levels of specific PUFAs in an individual.

PUFAs, or derivatives thereof, made by the disclosed method can be used as dietary supplements, particularly in infant formulas, for patients undergoing intravenous feeding or for preventing or treating malnutrition. Particular fatty acids such as EPA are used to alter the composition of infant formulas to better replicate the PUFA composition of human breast milk. The predominant triglyceride in human milk has been reported to be 1,3-di-oleoyl-2-palmitoyl, with 2-palmitoyl glycerides reported as better absorbed than 2-oleoyl or 2-lineoyl glycerides (U.S. Pat. No. 4,876,107). Typically, human breast milk has a fatty acid profile comprising from about 0.15% to about 0.36% as DHA, from about 0.03% to about 0.13% as EPA, from about 0.30% to about 0.88% as ARA, from about 0.22% to about 0.67% as DGLA, and from about 0.27% to about 1.04% as GLA. A preferred ratio of GLA:DGLA:ARA in infant formulas is from about 1:1:4 to about 1:1:1, respectively. Amounts of oils providing these ratios of PUFA can be determined without undue experimentation by one of skill in the art. PUFAS, or host cells containing them, also can be used as animal food supplements to alter an animal's tissue or milk fatty acid composition to one more desirable for human or animal consumption.

For dietary supplementation, the purified PUFAs, or derivatives thereof, may be incorporated into cooking oils, fats or margarines formulated so that in normal use the recipient would receive the desired amount. The PUFAs may also be incorporated into infant formulas, nutritional supplements or other food products, and may find use as anti-inflammatory or cholesterol lowering agents.

For pharmaceutical use (human or veterinary), the compositions are generally administered orally but can be administered by any route by which they may be successfully absorbed, e.g., parenterally (i.e. subcutaneously, intramuscularly or intravenously), rectally or vaginally or topically, for example, as a skin ointment or lotion. Where available, gelatin capsules are the preferred form of oral administration. Dietary supplementation as set forth above can also provide an oral route of administration. The unsaturated acids of the present invention may be administered in conjugated forms, or as salts, esters, amides or prodrugs of the fatty acids. Any pharmaceutically acceptable salt is encompassed by the present invention; especially preferred are the sodium, potassium or lithium salts. Also encompassed are the N-alkylpolyhydroxamine salts, such as N-methyl glucamine, described in PCT publication WO 96/33155. Preferred esters are the ethyl esters.

The PUFAs of the present invention may be administered alone or in combination with a pharmaceutically acceptable carrier or excipient. As solid salts, the PUFAs can also be administered in tablet form. For intravenous administration, the PUFAs or derivatives thereof may be incorporated into commercial formulations such as Intralipids. Where desired, the individual components of formulations may be individually provided in kit form, for single or multiple use. A typical dosage of a particular fatty acid is from 0.1 mg to 20 g, or even 100 g daily, and is preferably from 10 mg to 1, 2, 5 or 10 g daily as required, or molar equivalent amounts of derivative forms thereof. Parenteral nutrition compositions comprising from about 2 to about 30 weight percent fatty acids calculated as triglycerides are encompassed by the present invention; especially preferred is a composition having from about 1 to about 25 weight percent of the total fatty acid composition as GLA (U.S. Pat. No. 5,196,198). Other vitamins, and particularly fat-soluble vitamins such as vitamin A, D, E and L-carnitine can optionally be included. Where desired, a preservative such as α tocopherol may be added, typically at about 0.1% by weight. The typical normal adult plasma fatty acid profile comprises 6.64 to 9.46% of ARA, 1.45 to 3.11% of DGLA, and 0.02 to 0.08% of GLA. These PUFAs or their metabolic precursors can be administered, either alone or in mixtures with other PUFAs, to achieve a normal fatty acid profile in a patient.

The following examples are presented by way of illustration, not of limitation.

EXAMPLES

Example 1 Isolation of Δ5 Desaturase Nucleotide Sequence from *Mortierella alpina*

Example 2 Isolation of Δ6 Desaturase Nucleotide Sequence from *Mortierella alpina*

Example 3 Identification of Δ6 Desaturases Homologous to the *Mortierella alpina* Δ6 Desaturase Example 4 Isolation of Δ12 Desaturase Nucleotide Sequence from *Mortierella alpina*

Example 5 Isolation of Cytochrome b5 Reductase Nucleotide Sequence from *Mortierella alpina*

Example 6 Expression of *M. alpina* Desaturase Clones in Baker's Yeast

Example 7 Fatty Acid Analysis of Leaves from Ma29 Transgenic Brassica Plants

Example 8 Expression of *M. alpina* Δ6 Desaturase in *Brassica napus*

Example 1

Isolation of a Δ5-Desaturase Nucleotide Sequence from *Mortierella alpina*

*Motierella alpina* produces arachidonic acid (ARA, 20:4) from the precursor 20:3 by a Δ5-desaturase. A nucleotide sequence encoding the Δ5-desaturase from *Mortierella alpina* (see FIG. 7) was obtained through PCR amplification using *M. alpina* 1$^{st}$ strand cDNA and degenerate oligonucleotide primers corresponding to amino acid sequences conserved between Δ6-desaturases from Synechocystis and Spirulina. The procedure used was as follows:

Total RNA was isolated from a 3 day old PUFA-producing culture of *Mortierella alpina* using the protocol of Hoge et al. (1982) *Experimental Mycology* 6:225–232. The RNA was used to prepare double-stranded cDNA using BRL's lambda-ZipLox system, following the manufacturer's instructions. Several size fractions of the *M. alpina* cDNA were packaged separately to yield libraries with different average-sized inserts. The "full-length" library contains approximately 3×10$^6$ clones with an average insert size of 1.77 kb. The "sequencing-grade" library contains approximately 6×10$^5$ clones with an average insert size of 1.1 kb.

Figure 8A:
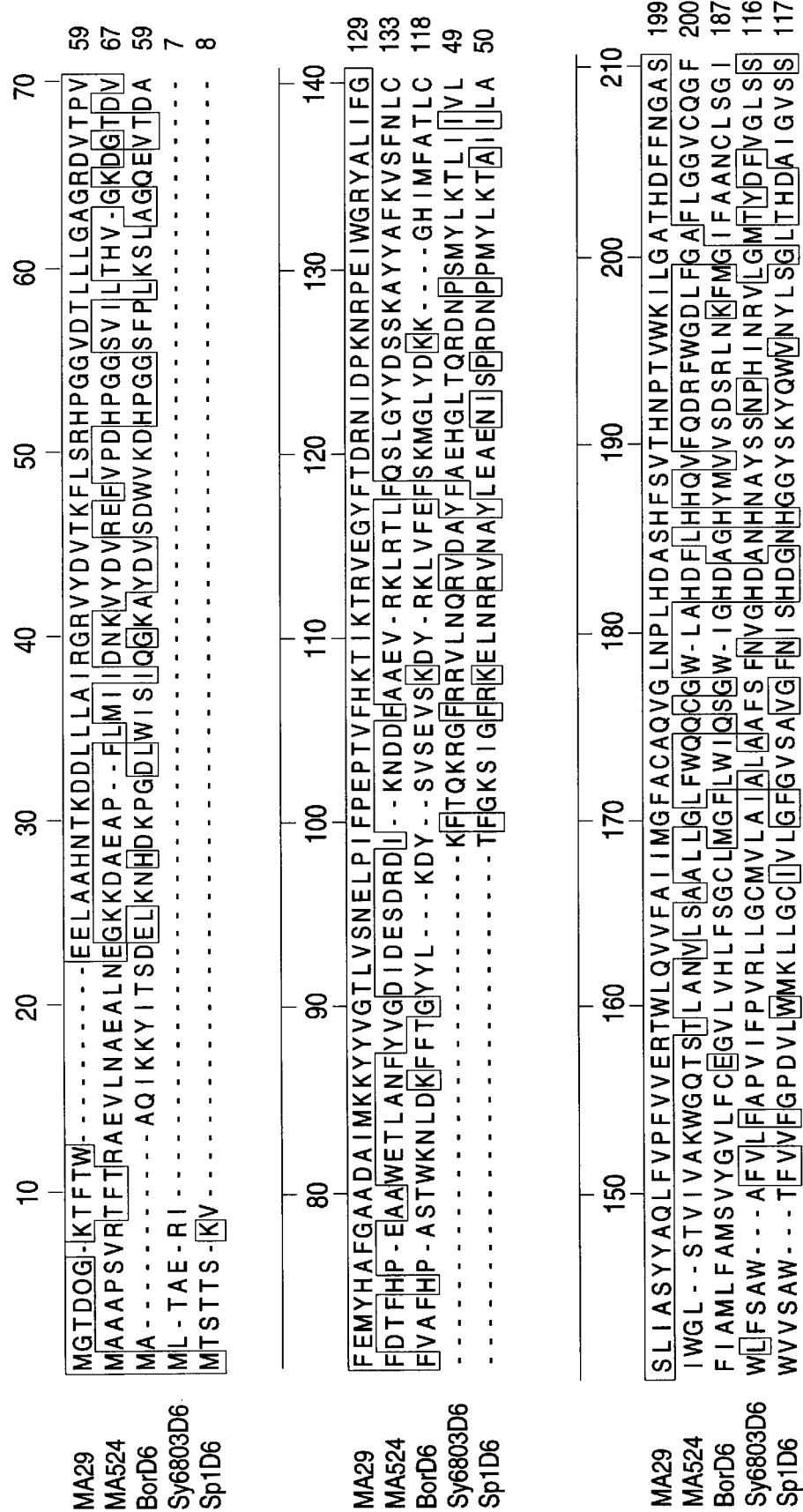
FIG. 8 shows alignments of the protein sequence of the $\Delta 5$ desaturase (SEQ ID NO:6) with $\Delta 6$ desaturases (SEQ ID NO:2) and related sequences (SEQ ID NOS: 16, 17, 18).
Figure 8B:
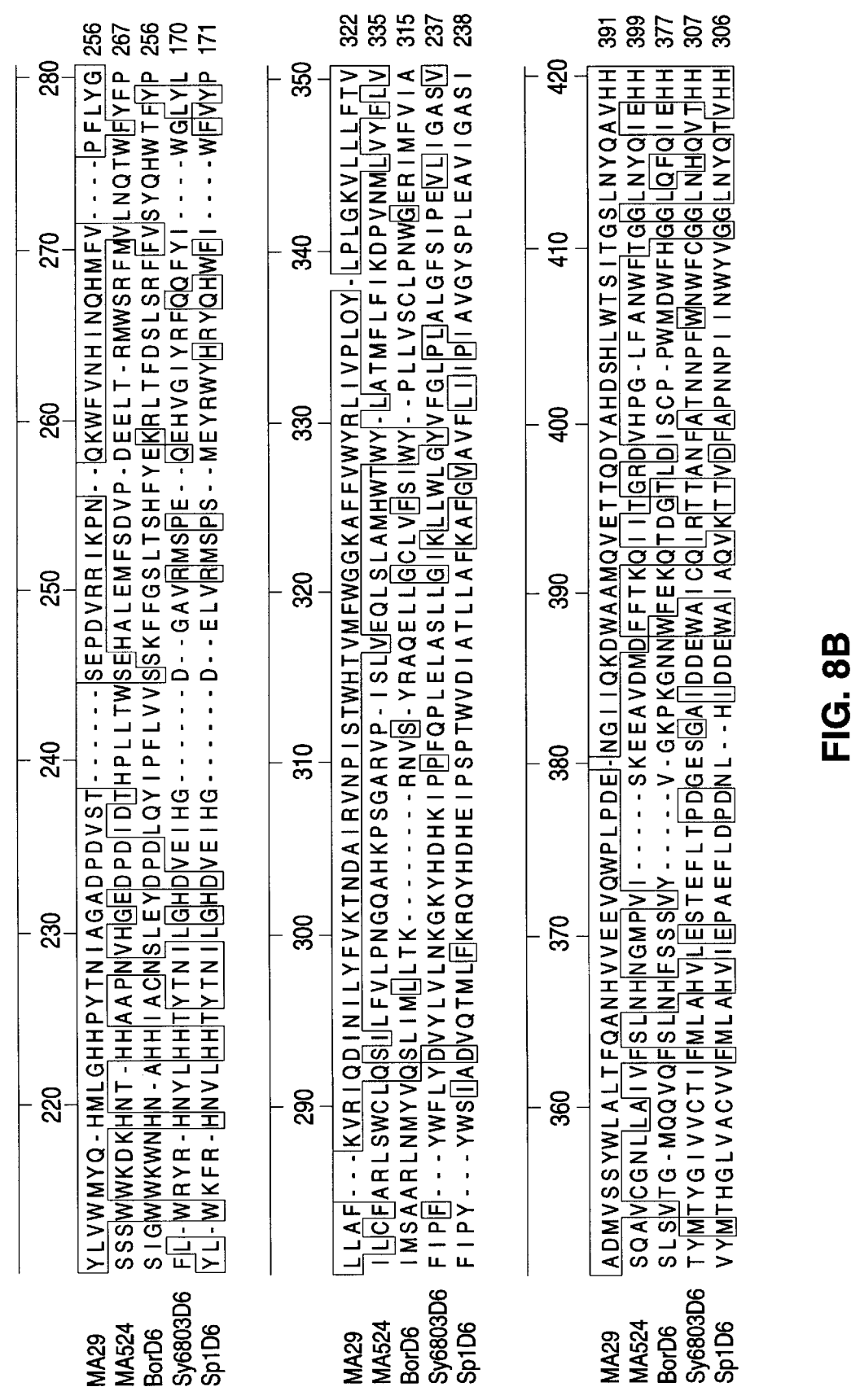

5 μg of total RNA was reverse transcribed using BRL Superscript RTase and the primer TSyn 5'-CCAAGCTTCTGCAGGAGCTCTTTTTTTTTTTTT-3', SEQ ID NO:19. Degenerate oligonucleotides were designed to regions conserved between the two cyanobacterial Δ6-desaturase sequences. The specific primers used were D6DESAT-F3 5'-CUACUACUACUACAYCAYACHTAYACNAAYAT-3', SEQ ID NO:20 and D6DESAT-R3 5'-CAUCAUCAUCAUNGGRAANARRTGRTG-3', SEQ ID NO:21, where Y=C+T, R=A+G, and N=Inosine+C. PCR amplification was carried out in a 25 μl volume containing: template derived from 40 ng total RNA, 2 pM each primer, 200 μM each deoxyribonucleotide triphosphate, 60 mM Tris-Cl, pH 8.5, 15 mM (NH$_4$)$_2$SO$_4$, 2 mM MgCl$_2$. Samples were subjected to an initial desaturation step of 95 degrees (all temperatures Celsius) for 5 minutes, then held at 72 degrees while 0.2 U of Taq polymerase were added. PCR thermocycling conditions were as follows: 94 degrees for 1 min., 45 degrees for 1.5 min., 72 degrees for 2 min. PCR was continued for 35 cycles. PCR using these primers on the *M. alpina* first-strand cDNA produced a 550 bp reaction product. Comparison of the deduced amino acid sequence of the *M. alpina* PCR fragment (see FIG. 6) revealed regions of homology with Δ6-desaturases (see FIG. 8). However, there was only about 28% identity over the region compared.

The PCR product was used as a probe to isolate corresponding cDNA clones from a *M. alpina* library. The longest cDNA clone, Ma29, was designated pCGN5521 and has been completely sequenced on both strands. The cDNA is contained as a 1481 bp insert in the vector pZL1 (Bethesda Research Laboratories) and, beginning with the first ATG, contains an open reading frame encoding 446 amino acids. The reading frame contains the sequence deduced from the PCR fragment. The sequence of the cDNA insert was found to contain regions of homology to Δ6-desaturases (see FIG. 8). For example, three conserved "histidine boxes" (that have been observed in all other membrane-bound desaturases (Okuley et al., (1994) *The Plant Cell* 6:147–158)) were found to be present in the Mortierella sequence at amino acid positions 171–175, 207–212, and 387–391 (see FIGS. 5A–5D). However, the typical "HXXHH" (SEQ ID NO:15) amino acid motif for the third histidine box for the Mortierella desaturase was found to be QXXHH (SEQ ID NO:24). Surprisingly, the amino-terminus of the encoded protein, showed significant homology to cytochrome b5 proteins. Thus, the Mortierella cDNA clone appears to represent a fusion between a cytochrome b5 and a fatty acid desaturase. Since cytochrome b5 is believed to function as the electron donor for membrane-bound desaturase enzymes, it is possible that the N-terminal cytochrome b5 domain of this desaturase protein is involved in its function. This may be advantageous when expressing the desaturase in heterologous systems for PUFA production.

Example 2

Isolation of Δ6 Desaturase Nucleotide Sequence from *Mortierella alpina*

A nucleic acid sequence from a partial cDNA clone, Ma524, encoding a Δ6 fatty acid desaturase from *Mortierella alpina* was obtained by random sequencing of clones from the *M. alpina* cDNA library described in Example 1. cDNA-containing plasmids were excised as follows:

Five μl of phage were combined with 100 μl of *E. coli* DH10B(ZIP) grown in ECLB plus 10 μg/ml kanamycin, 0.2% maltose, and 10 mM MgSO$_4$ and incubated at 37 degrees for 15 minutes. 0.9 ml SOC was added and 100 μl of the bacteria immediately plated on each of 10 ECLB+50 μg Pen plates. No 45 minute recovery time was needed. The plates were incubated overnight at 37 degrees. Colonies were picked into ECLB+50 μg Pen media for overnight cultures to be used for making glycerol stocks and miniprep DNA. An aliquot of the culture used for the miniprep is stored as a glycerol stock. Plating on ECLB+50 μg Pen/ml resulted in more colonies and a greater proportion of colonies containing inserts than plating on 100 μg/ml Pen.

Random colonies were picked and plasmid DNA purified using Qiagen miniprep kits. DNA sequence was obtained from the 5' end of the cDNA insert and compared to the databases using the BLAST algorithm. Ma524 was identified as a putative Δ6 desaturase based on DNA sequence homology to previously identified Δ6 desaturases. A full-length cDNA clone was isolated from the *M. alpina* library. The abundance of this clone appears to be slightly (2×) less than Ma29. Ma524 displays significant homology to a portion of a *Caenorhabditis elegans* cosmid, WO6D2.4, a cytochrome b5/desaturase fusion protein from sunflower, and the two Δ6 desaturases in the public databanks those from Synechocystis and Spirulina.

In addition, Ma524 shows significant homology to the borage Δ6-desaturase sequence (PCT publication WO 96/21022). Ma524 thus appears to encode a Δ6-desaturase that is related to the borage and algal Δ6-desaturases. It should be noted that, although the amino acid sequences of Ma524 and the borage Δ6 denaturases are similar, the base composition of the cDNAs is quite different: the borage cDNA has an overall base composition of 60% A+T, with some regions exceeding 70%, while Ma524 has an average of 44% A+T base composition, with no regions exceeding 60%. This may have implications for expressing the cDNAs in microorganisms or animals which favor different base compositions. It is known that poor expression of recombinant genes can occur when the host has a very different base composition from that of the introduced gene. Speculated mechanisms for such poor expression include decreased stability or translatability of the mRNA.

Example 3

Identification of Δ6-Desaturases Homologous to the *Mortierella alpina* Δ6-Desaturase Nucleic acid sequences that encode putative Δ6-desaturases were identified through a BLASTX search of the est databases through NCBI using the Ma524 amino acid sequence. Several sequences showed significant homology. In particular, the deduced amino acid sequence of two *Arabidopsis thaliana* sequences, (accession numbers F13728 and T42806) showed homology to two different regions of the deduced amino acid sequence of Ma524. The following PCR primers were designed: ATTS4723-FOR (complementary to F 13728) 5'-CUACUACUACUAGGAGTCCTCTACGGTGTTTTG, SEQ ID NO:22, and T42806-REV (complementary to T42806) 5' CAUCAUCAUCAUATGATGCTCAAGCTGAAACTG, SEQ ID NO:23. Five μg of total RNA isolated from developing siliques of *Arabidopsis thaliana* was reverse transcribed using BRL Superscript RTase and the primer TSyn 5'-CCAAGCTTCTGCAGGAGCTTTTTTTTTTTTTT-3', SEQ ID NO:24. PCR was carried out in a 50 μl volume containing: template derived from 25 ng total RNA, 2 pM each primer, 200 μM each deoxyribonucleotide triphosphate, 60 mM Tris-Cl, pH 8.5, 15 mM $(NH_4)_2SO_4$, 2 mM $MgCl_2$, 0.2 U Taq Polymerase. Cycle conditions were as follows: 94 degrees for 30 sec., 50 degrees for 30 sec., 72 degrees for 30 sec. PCR was continued for 35 cycles followed by an additional extension at 72 degrees for 7 minutes. PCR resulted in a fragment of ~750 base pairs which was subsequently subcloned, named 12-5, and sequenced. Each end of this fragment corresponds to the Arabidopsis est from which the PCR primers were derived. This is the sequence named 12-5. The deduced amino acid sequence of 12-5 is compared to that of Ma524 and ests from human W28140 (SEQ ID NO:10), mouse W53753 (SEQ ID NO:12), and *C. elegans* R05219 (SEQ ID NO:11) in FIG. 4. Based on homology, these sequences represent desaturase polypeptides. The full-length genes can be cloned using probes based on the est sequences. The genes can then be placed in expression vectors and expressed in host cells and their specific Δ6- or other desaturase activity can be determined as described below.

Example 4

Isolation of Δ12 Desaturase Nucleotide Sequence from *Mortierella alpina*

Based on the fatty acids it accumulates, *Mortierella alpina* has an ω6 type desaturase. The ω6 desaturase is responsible for the production of linoleic acid (18:2) from oleic acid (18:1). Linoleic acid (18:2) is a substrate for a Δ6 desaturase. This experiment was designed to determine if *Mortierella alpina* has a Δ12-desaturase polypeptide, and if so, to identify the corresponding nucleotide sequence. A random colony from the *M. alpina* sequencing grade library, Ma648, was sequenced and identified as a putative desaturase based on DNA sequence homology to previously identified desaturases, as described for Ma524 (see Example 2). The deduced amino acid sequence from the 5' end of the Ma648 cDNA displays significant homology to soybean microsomal ω6 (12) desaturase (accession #L43921) as well as castor bean oleate 12-hydroxylase (accession #U22378). In addition, homology is observed to a variety of other ω6 (Δ12) and ω3 (Δ15) fatty acid desaturase sequences.

Example 5

Isolation of Cytochrome b5 Reductase Nucleotide Sequence from *Mortierella alpina*

A nucleic acid sequence encoding a cytochrome b5 reductase from *Mortierella alpina* was obtained as follows. A cDNA library was constructed based on total RNA isolated from *Mortierella alpina* as described in Example 1. DNA sequence was obtained from the 5' and 3' ends of one of the clones, M12-27. A search of public databanks with the deduced amino acid sequence of the 3' end of M12-27 (see FIG. 5) revealed significant homology to known cytochrome b5 reductase sequences. Specifically, over a 49 amino acid region, the Mortierella clone shares 55% identity (73% homology) with a cytochrome b5 reductase from pig (see FIG. 4).

Example 6

Expression of *M. alpina* Desaturase Clones in Baker's Yeast

Yeast Transformation

Lithium acetate transformation of yeast was performed according to standard protocols (*Methods in Enzymology*, Vol. 194, p. 186–187, 1991). Briefly, yeast were grown in YPD at 30° C. Cells were spun down, resuspended in TE, spun down again, resuspended in TE containing 100 mM lithium acetate, spun down again, and resuspended in TE/lithium acetate. The resuspended yeast were incubated at 30° C. for 60 minutes with shaking. Carrier DNA was added, and the yeast were aliquoted into tubes. Transforming DNA was added, and the tubes were incubated for 30 min. at 30° C. PEG solution (35% (w/v) PEG 4000, 100 mM lithium acetate, TE pH7.5) was added followed by a 50 min. incubation at 30° C. A 5 min. heat shock at 42° C. was performed, the cells were pelleted, washed with TE, pelleted again and resuspended in TE. The resuspended cells were then plated on selective media.

Desaturase Expression in Transformed Yeast cDNA clones from *Mortierella alpina* were screened for desaturase activity in baker's yeast. A canola Δ15-desaturase (obtained by PCR using $1^{st}$ strand cDNA from *Brassica napus* cultivar 212/86 seeds using primers based on the published sequence (Arondel et al. *Science* 258:1353–1355)) was used as a positive control. The Δ15-desaturase gene and the gene from cDNA clone Ma29 was put in the expression vector pYES2 (Invitrogen), resulting in plasmids pCGR-2 and pCGR-4, respectively. These plasmids were transfected into *S. cerevisiae* yeast strain 334 and expressed after induction with galactose and in the presence of substrates that allowed detection of specific desaturase activity. The control strain was *S. cerevisiae* strain 334 containing the unaltered pYES2 vector. The substrates used, the products produced and the indicated desaturase activity were: DGLA (conversion to ARA would indicate Δ5-desaturase activity), linoleic acid (conversion to GLA would indicate Δ6-desaturase activity; conversion to ALA would indicate Δ15-desaturase activity), oleic acid (an endogenous substrate made by *S. cerevisiae*, conversion to linoleic acid would indicate Δ12-desaturase activity, which *S. cerevisiae* lacks), or ARA (conversion to EPA would indicate Δ17-desaturase activity). The results are provided in Table 1 below. The lipid fractions were extracted as follows: Cultures were grown for 48–52 hours at 15° C. Cells were pelleted by centrifugation, washed once with sterile $ddH_2O$, and repelleted. Pellets were vortexed with methanol; chloroform was added along with tritridecanoin (as an internal standard). The mixtures were incubated for at least one hour at room temperature or at 4° C. overnight. The chloroform layer was extracted and filtered through a Whatman filter with one gram of anhydrous sodium sulfate to remove particulates and residual water. The organic solvents were evaporated at 40° C. under a stream of nitrogen. The extracted lipids were then derivatized to fatty acid methyl esters (FAME) for gas chromatography analysis (GC) by adding 2 ml of 0.5N potassium hydroxide in methanol to a closed tube. The samples were heated to 95° C. to 100° C. for 30 minutes and cooled to room temperature. Approximately 2 ml of 14% boron trifluoride in methanol was added and the heating repeated. After the extracted lipid mixture cooled, 2 ml of water and 1 ml of hexane were added to extract the FAME for analysis by GC. The percent conversion was calculated by dividing the product produced by the sum of (the product produced and the substrate added) and then multiplying by 100. To calculate the oleic acid percent conversion, as no substrate was added, the total linoleic acid produced was divided by the sum of (oleic acid and linoleic acid produced), then multiplying by 100.

TABLE 1

*M. alpina* Desaturase Expression in Baker's Yeast

| CLONE | ENZYME ACTIVITY | % CONVERSION OF SUBSTRATE |
|---|---|---|
| pCGR-2 | Δ6 | 0 (18:2 to 18:3ω6) |
| (canola Δ15 | Δ15 | 16.3 (18:2 to 18:3ω3) |
| desaturase) | Δ5 | 2.0 (20:3 to 20:4ω6) |
|  | Δ17 | 2.8 (20:4 to 20:5ω3) |

TABLE 1-continued

*M. alpina* Desaturase Expression in Baker's Yeast

| CLONE | ENZYME ACTIVITY | % CONVERSION OF SUBSTRATE |
|---|---|---|
|  | Δ12 | 1.8 (18:1 to 18:2ω6) |
| pCGR-4 | Δ6 | 0 |
| (*M. alpina* | Δ15 | 0 |
| Δ6-like, Ma29) | Δ5 | 15.3 |
|  | Δ17 | 0.3 |
|  | Δ12 | 3.3 |
| pCGR-7 | Δ6 | 0 |
| (*M. alpina* | Δ15 | 3.8 |
| Δ12-like, Ma648 | Δ5 | 2.2 |
|  | Δ17 | 0 |
|  | Δ12 | 63.4 |

The Δ15-desaturase control clone exhibited 16.3% conversion of the substrate. The pCGR-5 clone expressing the Ma29 cDNA converted 15.3% of the 20:3 substrate to 20:4 ω6, indicating that the gene encodes a Δ5-desaturase. The background (non-specific conversion of substrate) was between 0–3% in these cases. The pCGR-5 clone expressing the Ma524 cDNA showed 6% conversion of the substrate to GLA, indicating that the gene encodes a Δ6-desaturase. The pCGR-7 clone expressing the Ma648 cDNA converted 63.4% conversion of the substrate to LA, indicating that the gene encodes a Δ12-desaturase. Substrate inhibition of activity was observed by using different concentrations of the substrate. When substrate was added to 100 μM, the percent conversion to product dropped as compared to when substrate was added to 25 μM (see below). These data show that desaturases with different substrate specificities can be expressed in a heterologous system and used to produce PUFAs.

Table 2 represents fatty acids of interest as a percent of the total lipid extracted from the yeast host *S. cerevisiae* 334 with the indicated plasmid. No glucose was present in the growth media. Affinity gas chromatography was used to separate the respective lipids. GC/MS was employed to verify the identity of the product(s). The expected product for the *B. napus* Δ15-desaturase, α-linolenic acid, was detected when its substrate, linoleic acid, was added exogenously to the induced yeast culture. This finding demonstrates that yeast expression of a desaturase gene can produce functional enzyme and detectable amounts of product under the current growth conditions. Both exogenously added substrates were taken up by yeast, although slightly less of the longer chain PUFA, dihomo-γ-linolenic acid (20:3), was incorporated into yeast than linoleic acid (18:2) when either was added in free form to the induced yeast cultures. γ-linolenic acid was detected when linoleic acid was present during induction and expression of *S. cerevisiae* 334 (pCGR-5). The presence of this PUFA demonstrates Δ6-desaturase activity from pCGR-5 (MΔ524). Linoleic acid, identified in the extracted lipids from expression of *S. cerevisiae* 334 (pCGR-7), classifies the cDNA MΔ648 from *M. alpina* as the Δ12-desaturase.

TABLE 2

Fatty Acid as a Percentage of Total Lipid Extracted from Yeast

| Plasmid in Yeast (enzyme) | 18:2 Incorporated | α-18:3 Produced | γ-18:3 Produced | 20:3 Incorporated | 20:4 Produced | 18:1* Present | 18:2 Produced |
|---|---|---|---|---|---|---|---|
| pYES2 (control) | 66.9 | 0 | 0 | 58.4 | 0 | 4 | 0 |
| pCGR-2 (Δ15) | 60.1 | 5.7 | 0 | 50.4 | 0 | 0.7 | 0 |
| pCGR-4 (Δ5) | 67 | 0 | 0 | 32.3 | 5.8 | 0.8 | 0 |
| pCGR-5 (Δ6) | 62.4 | 0 | 4.0 | 49.9 | 0 | 2.4 | 0 |
| pCGR-7 (Δ12) | 65.6 | 0 | 0 | 45.7 | 0 | 7.1 | 12.2 |

100 μM substrate added
*18:1 is an endogenous fatty acid in yeast
Key To Tables
18:1 = oleic acid
18:2 = linoleic acid
α-18:3 = α-linolenic acid
γ-18:3 = γ-linolenic acid
18:4 = stearidonic acid
20:3 = dihomo-γ-linolenic acid
20:4 = arachidonic acid

Example 7

Expression of Δ5 Desaturase in Plants

Expression in Leaves This experiment was designed to determine whether leaves expressing Ma29 (as determined by Northern) were able to convert exogenously applied DGLA (20:3) to ARA (20:4).

The Ma29 desaturase cDNA was modified by PCR to introduce convenient restriction sites for cloning. The desaturase coding region has been inserted into a d35 cassette under the control of the double 35S promoter for expression in Brassica leaves (pCGN5525) following standard protocols (see U.S. Pat. Nos. 5,424,200 and 5,106,739). Transgenic Brassica plants containing pCGN5525 were generated following standard protocols (see U.S. Pat. Nos. 5,188,958 and 5,463,174).

In the first experiment, three plants were used: a control, LPOO4-1, and two transgenics,, 5525-23 and 5525-29. LP004 is a low-linolenic Brassica variety. Leaves of each were selected for one of three treatments: water, GLA or DGLA. GLA and DGLA were purchased as sodium salts from NuChek Prep and dissolved in water at 1 mg/ml. Aliquots were capped under $N_2$ and stored at −70 degrees C. Leaves were treated by applying a 50 μl drop to the upper surface and gently spreading with a gloved finger to cover the entire surface. Applications were made approximately 30 minutes before the end of the light cycle to minimize any photooxidation of the applied fatty acids. After 6 days of treatment one leaf from each treatment was harvested and cut in half through the mid rib. One half was washed with water to attempt to remove unincorporated fatty acid. Leaf samples were lyophilized overnight, and fatty acid composition determined by gas chromatography (GC). The results are shown in Table 3.

TABLE 3

Fatty Acid Analysis of Leaves from Ma29 Transgenic Brassica Plants

| Treatment | SPL # | 16:00 % | 16:01 % | 18:00 % | 18:01 % | 18:1o % | 18:1v % | 18:02 % | 18:3g % | 18:03 % | 18:04 % | 20:00 % | 20:01 % |
|---|---|---|---|---|---|---|---|---|---|---|---|---|---|
| Water | 33 | 12.95 | 0.08 | 2.63 | 2.51 | 1.54 | 0.98 | 16.76 | 0 | 45.52 | 0 | 0.09 | 0 |
|  | 34 | 13.00 | 0.09 | 2.67 | 2.56 | 1.55 | 1.00 | 16.86 | 0 | 44.59 | 0 | 0.15 | 0 |
|  | 35 | 14.13 | 0.09 | 2.37 | 2.15 | 1.27 | 0.87 | 16.71 | 0 | 49.91 | 0 | 0.05 | 0.01 |
|  | 36 | 13.92 | 0.08 | 2.32 | 2.07 | 1.21 | 0.86 | 16.16 | 0 | 50.25 | 0 | 0.05 | 0 |
|  | 37 | 13.79 | 0.11 | 2.10 | 2.12 | 1.26 | 0.86 | 15.90 | 0.08 | 46.29 | 0 | 0.54 | 0.01 |
|  | 38 | 12.80 | 0.09 | 1.94 | 2.08 | 1.35 | 0.73 | 14.54 | 0.11 | 45.61 | 0 | 0.49 | 0.01 |
| GLA | 39 | 12.10 | 0.09 | 2.37 | 2.10 | 1.29 | 0.82 | 14.85 | 1.63 | 43.66 | 0 | 0.53 | 0 |
|  | 40 | 12.78 | 0.10 | 2.34 | 2.22 | 1.36 | 0.86 | 15.29 | 1.72 | 47.22 | 0 | 0.50 | 0.02 |
|  | 41 | 13.71 | 0.07 | 2.68 | 2.16 | 1.34 | 0.82 | 15.92 | 2.12 | 46.55 | 0 | 0.09 | 0 |
|  | 42 | 14.10 | 0.07 | 2.75 | 2.35 | 1.51 | 0.84 | 16.66 | 1.56 | 46.41 | 0 | 0.09 | 0.01 |
|  | 43 | 13.62 | 0.09 | 2.22 | 1.94 | 1.21 | 0.73 | 14.68 | 2.42 | 46.69 | 0 | 0.51 | 0.01 |
|  | 44 | 13.92 | 0.09 | 2.20 | 2.17 | 1.32 | 0.85 | 15.22 | 2.30 | 46.05 | 0 | 0.53 | 0.02 |
| DGLA | 45 | 12.45 | 0.14 | 2.30 | 2.28 | 1.37 | 0.91 | 15.65 | 0.07 | 44.62 | 0 | 0.12 | 0.01 |
|  | 46 | 12.67 | 0.15 | 2.69 | 2.50 | 1.58 | 0.92 | 15.96 | 0.09 | 42.77 | 0 | 0.56 | 0.01 |
|  | 47 | 12.56 | 0.23 | 3.40 | 1.98 | 1.13 | 0.86 | 13.57 | 0.03 | 45.52 | 0 | 0.51 | 0.01 |
|  | 48 | 13.07 | 0.24 | 3.60 | 2.51 | 1.63 | 0.88 | 13.54 | 0.04 | 45.13 | 0 | 0.50 | 0.01 |

TABLE 3-continued

Fatty Acid Analysis of Leaves from Ma29 Transgenic Brassica Plants

| | 49 | 13.26 | 0.07 | 2.81 | 2.34 | 1.67 | 0.67 | 16.04 | 0.04 | 43.89 | 0 | 0.59 | 0 |
| | 50 | 13.53 | 0.07 | 2.84 | 2.41 | 1.70 | 0.70 | 16.07 | 0.02 | 44.90 | 0 | 0.60 | 0.01 |

| Treatment | SPL # | 20:02 % | 20:03 % | 20:04 % | 20:05 % | 22:00 % | 22:01 % | 22:02 % | 22:03 % | 22:06 % | 24:0 % | 24:1 % |
|---|---|---|---|---|---|---|---|---|---|---|---|---|
| Water | 33 | 0 | 0 | 0.29 | 0 | 0.01 | 0.09 | 16.26 | 0 | 0 | 0.38 | 0.18 |
| | 34 | 0.01 | 0 | 0.26 | 0 | 0.14 | 0.10 | 16.82 | 0.02 | 0.05 | 0.36 | 0.27 |
| | 35 | 0.01 | 0 | 0.25 | 0 | 0.12 | 0.06 | 11.29 | 0.04 | 0.05 | 0.29 | 0.25 |
| | 36 | 0 | 0.01 | 0.26 | 0 | 0.07 | 0.04 | 11.82 | 0.03 | 0.36 | 0.28 | 0.21 |
| | 37 | 0.02 | 0 | 0.21 | 0 | 0.18 | 0.08 | 15.87 | 0.06 | 0.20 | 0.30 | 0.17 |
| | 38 | 0.01 | 0 | 0.24 | 0 | 0.15 | 0.07 | 13.64 | 0.09 | 0.08 | 5.89 | 0.23 |
| GLA | 39 | 0.02 | 0.01 | 0.27 | 0 | 0.10 | 0.08 | 16.25 | 3.42 | 0.19 | 0.37 | 0.17 |
| | 40 | 0.01 | 0 | 0.27 | 0 | 0.10 | 0.10 | 14.74 | 0.05 | 0.10 | 0.36 | 0.14 |
| | 41 | 0 | 0 | 0.27 | 0 | 0.20 | 0.10 | 13.15 | 0.13 | 0.29 | 0.33 | 0.20 |
| | 42 | 0 | 0 | 0.28 | 0 | 0.11 | 0.11 | 12.60 | 0.02 | 0.24 | 0.38 | 0.13 |
| | 43 | 0.01 | 0 | 0.28 | 0 | 0.10 | 0.03 | 14.73 | 0.01 | 0.24 | 0.34 | 0.14 |
| | 44 | 0.02 | 0 | 0.26 | 0 | 0.13 | 0.07 | 14.43 | 0.05 | 0.16 | 0.33 | 0.17 |
| DGLA | 45 | 0.06 | 1.21 | 0.26 | 0 | 0.07 | 0.07 | 18.67 | 0.02 | 0.21 | 0.36 | 0.13 |
| | 46 | 0 | 1.94 | 0.27 | 0 | 0.11 | 0.09 | 17.97 | 0.09 | 0.39 | 0.41 | 0.11 |
| | 47 | 0.01 | 0.69 | 0.96 | 0 | 0.11 | 0.07 | 17.96 | 0 | 0.22 | 0.49 | 0.20 |
| | 48 | 0.01 | 0.70 | 0.74 | 0 | 0.14 | 0.09 | 17.14 | 0.05 | 0.32 | 0.52 | 0.10 |
| | 49 | 0 | 0.35 | 1.11 | 0 | 0.10 | 0.07 | 17.26 | 0.07 | 0.23 | 0.39 | 0.18 |
| | 50 | 0 | 0.20 | 0.87 | 0 | 0.21 | 0.07 | 15.73 | 0.04 | 0.15 | 0.37 | 0.18 |

Leaves treated with GLA contained from 1.56 to 2.4 wt. % GLA. The fatty acid analysis showed that the lipid composition of control and transgenic leaves was essentially the same. Leaves of control plants treated with DGLA contained 1.2–1.9 wt. % DGLA and background amounts of ARA (0.26–0.27 wt. %). Transgenic leaves contained only 0.2–0.7 wt. % DGLA, but levels of ARA were increased (0.74–1.1 wt. %) indicating that the DGLA was converted to ARA in these leaves.

Expression in Seed

The purpose of this experiment was to determine whether a construct with the seed specific napin promoter would enable expression in seed.

The Ma29 cDNA was modified by PCR to introduce XhoI cloning sites upstream and downstream of the start and stop codons, respectively, using the following primers:

Madxho-forward:

5'-CUACUACUACUACUACTCGAGCAAGATGG-
GAACGGACCAAGG (SEQ ID NO:25)

Madxho-reverse:

5'-CAUCAUCAUCAUCTCGAGCTACTCTTC-
CTTGGGACGGAG (SEQ ID NO:26).

The PCR product was subcloned into pAMP1 (GIBCOBRL) using the CloneAmp system (GIBCOBRL) to create pCGN5522 and the Δ5 desaturase sequence was verified by sequencing of both strands.

For seed-specific expression, the Ma29 coding region was cut out of pCGN5522 as an XhoI fragment and inserted into the SalI site of the napin expression cassette, pCGN3223, to create pCGN5528. The HindIII fragment of pCGN5528 containing the napin 5' regulatory region, the Ma29 coding region, and the napin 3' regulatory region was inserted into the HindIII site of pCGN 1557 to create pCGN5531. pCGN5531 was introduced into *Brassica napus* cv.LP004 via Agrobacterium mediated transformation.

The fatty acid composition of twenty-seed pools of mature T2 seeds was analyzed by GC. Table 4 shows the results obtained with independent transformed lines as compared to non-transformed LP004 seed. The transgenic seeds containing pCGN5531 contain two fatty acids that are not present in the control seeds, tentatively identified as taxoleic acid (5,9-18:2) and pinolenic acid (5,9,12-18:3), based on their elution relative to oleic and linoleic acid. These would be the expected products of Δ5 desaturation of oleic and linoleic acids. No other differences in fatty acid composition were observed in the transgenic seeds.

TABLE 4

Composition of T2 Pooled Seed

| | 16:0 % | 16:1 % | 18:0 % | 18:1 % | (5,9)18:2 % | 18:2 % | (5,9,12)18:3 % | 18:3 % | 20:0 % | 20:1 % | 20:2 % | 22:0 % | 22:1 % | 24:0 % |
|---|---|---|---|---|---|---|---|---|---|---|---|---|---|---|
| LP004 control | 3.86 | 0.15 | 3.05 | 69.1 | 0 | 18.51 | 0.01 | 1.65 | 1.09 | 1.40 | 0.03 | 0.63 | 0.05 | 0.42 |
| 5531-1 | 4.26 | 0.15 | 3.23 | 62.33 | 4.07 | 21.44 | 0.33 | 1.38 | 0.91 | 1.04 | 0.05 | 0.41 | 0.03 | 0.27 |
| 5531-2 | 3.78 | 0.14 | 3.37 | 66.18 | 4.57 | 17.31 | 0.27 | 1.30 | 1.03 | 1.18 | 0 | 0.47 | 0.01 | 0.30 |
| 5531-6 | 3.78 | 0.13 | 3.47 | 63.61 | 6.21 | 17.97 | 0.38 | 1.34 | 1.04 | 1.14 | 0.05 | 0.49 | 0.02 | 0.26 |
| 5531-10 | 3.96 | 0.17 | 3.28 | 63.82 | 5.41 | 18.58 | 0.32 | 1.43 | 0.98 | 1.11 | 0.02 | 0.50 | 0 | 0.31 |
| 5531-16 | 3.91 | 0.17 | 3.33 | 64.31 | 5.03 | 18.98 | 0.33 | 1.39 | 0.96 | 1.11 | 0 | 0.44 | 0 | 0 |
| 5531-28 | 3.81 | 0.13 | 2.58 | 62.64 | 5.36 | 20.95 | 0.45 | 1.39 | 0.83 | 1.15 | 0.01 | 0.36 | 0.05 | 0.21 |

The purpose of this experiment is to determine whether a tandem binary construct containing two copies of the Ma29 desaturase with the seed specific napin promoter would provide for higher expression per genetic locus. A binary construct is prepared and transformed into LP004 Brassica plants as described above in Example 7.

Northern analysis is performed on plants to identify those expressing Ma29. Developing embryos are isolated approximately 25 days post anthesis or when the napin promoter is induced, and floated in a solution containing GLA or DGLA as described in Example 7. Fatty acid analysis of the embryos is then performed by GC to determine the amount of conversion of DGLA to ARA, following the protocol adapted for leaves in Example 7. The amount of ARA incorporated into triglycerides by endogenous Brassica acyl-transferasees is then evaluated by GC analysis as in Example 7.

Example 8

Expression of *M. alpina* Δ6 Desaturase in *Brassica napus*

The Ma524 cDNA was modified by PCR to introduce cloning sites using the following primers:
Ma524PCR-1

5'-CUACUACUACUAUCUAGACTCGAGAC-
CATGGCTGCTGCTCCAGTGTG (SEQ ID NO:27)

Ma524PCR-2

5'-CAUCAUCAUCAUAGGCCTCGAGTTACT-
GCGCCTTACCCAT (SEQ ID NO:28)

These primers allowed the amplification of the entire coding region and added XbaI and XhoI sites to the 5'-end and XhoI and StuI sites to the 3' end. The PCR product was subcloned into pAMP1 (GIBCOBRL) using the CloneAmp system (GIBCOBRL) to create pCGN5535 and the Δ6 desaturase sequence was verified by sequencing of both strands.

For seed-specific expression, the Ma524 coding region was cut out of pCGN5535 as an XhoI fragment and inserted into the SalI site of the napin expression cassette, pCGN3223, to create pCGN5536. The NotI fragment of pCGN5536 containing the napin 5' regulatory region, the Ma524 coding region, and the napin 3' regulatory region was inserted into the NotI site of pCGN1557 to create pCGN5538. pCGN5538 was introduced into *Brassica napus* cv.LP004 via Agrobacterium mediated transformation.

Maturing T2 seeds were collected from 6 independent transformation events in the greenhouse. The fatty acid composition of single seeds was analyzed by GC. Table 4 shows the results of control LP004 seeds and six 5538 lines. All of the 5538 lines except #8 produced seeds containing GLA. Presence of GLA segregated in these seeds as is expected for the T2 selfed seed population. In addition to GLA, the *M. aplina* Δ6 desaturase is capable of producing 18:4 (stearidonic) and another fatty acid believed to be the 6,9-18:2.

The above results show that desaturases with three different substrate specificities can be expressed in a heterologous system and used to produce poly-unsaturated long chain fatty acids. Exemplified were the production of ARA (20:4) from the precursor 20:3 (DGLA), the production of GLA (18:3) from 18:2 substrate, and the conversion of 18:1 substrate to 18:2, which is the precursor for GLA.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

TABLE 5

Fatty Acid Analysis of Seeds from Ma524 Transgenic Brassica Plants

| SPL # | 16:0 % | 16:1 % | 18:0 % | 18:1 | 5,9 18:2 % | 18:2 % | 18:3g % | 18:3 % | 18:4 % | 20:1 % | 22:0 % | 22:1 % | 24:0 % | 24:1 % |
|---|---|---|---|---|---|---|---|---|---|---|---|---|---|---|
| LP004-1 | 4.33 | 0.21 | 3.78 | 72.60 | 0 | 13.97 | 0 | 1.7 | 0 | 1.34 | 0.71 | 0.02 | 0.58 | 0.27 |
| -2 | 4.01 | 0.16 | 3.09 | 73.69 | 0 | 14.38 | 0.01 | 1.4 | 0 | 1.43 | 0.68 | 0.02 | 0.8 | 0.2 |
| -3 | 4.12 | 0.19 | 3.68 | 70.25 | 0 | 17.28 | 0 | 1.57 | 0 | 1.28 | 0.6 | 0.02 | 0.39 | 0.2 |
| -4 | 4.22 | 0.2 | 2.7 | 70.25 | 0 | 17.66 | 0 | 1.81 | 0 | 1.31 | 0.53 | 0.02 | 0.4 | 0.24 |
| -5 | 4.02 | 0.18 | 3.41 | 72.91 | 0 | 14.45 | 0.01 | 1.45 | 0 | 1.37 | 0.7 | 0.02 | 0.51 | 0.20 |
| -6 | 4.22 | 0.18 | 3.23 | 71.47 | 0 | 15.92 | 0.01 | 1.52 | 0 | 1.32 | 0.69 | 0.02 | 0.51 | 0.27 |
| -7 | 4.1 | 0.18 | 3.47 | 72.06 | 0 | 15.23 | 0 | 1.52 | 0 | 1.32 | 0.83 | 0.03 | 0.49 | 0.23 |
| -9 | 4.01 | 0.17 | 3.71 | 72.98 | 0 | 13.97 | 0.01 | 1.41 | 0 | 1.45 | 0.74 | 0.03 | 0.58 | 0.23 |
| -10 | 4.04 | 0.18 | 3.57 | 70.03 | 0 | 17.46 | 0 | 1.5 | 0 | 1.33 | 0.81 | 0.03 | 0.38 | 0.24 |
| 5536-1-1 | 4.81 | 0.2 | 3.48 | 68.12 | 1.37 | 10.68 | 7.48 | 1.04 | 0.33 | 1.19 | 0.49 | 0.02 | 0.33 | 0.13 |
| -2 | 4.81 | 0.22 | 3.46 | 68.84 | 1.38 | 10.28 | 7.04 | 1.01 | 0.31 | 1.15 | 0.48 | 0.02 | 0.39 | 0 |
| -3 | 4.78 | 0.24 | 3.24 | 68.86 | 0 | 21.38 | 0 | 1.49 | 0 | 1.08 | 0.48 | 0.02 | 0.38 | 0.22 |
| -4 | 4.84 | 0.3 | 3.69 | 67.64 | 1.67 | 9.9 | 8.97 | 1.02 | 0.38 | 1.14 | 0.53 | 0.02 | 0.5 | 0.18 |
| -5 | 4.64 | 0.2 | 3.58 | 65.5 | 3.81 | 8.85 | 10.14 | 0.95 | 0.48 | 1.19 | 0.47 | 0.01 | 0.33 | 0.12 |
| -6 | 4.01 | 0.27 | 3.44 | 86.51 | 1.48 | 11.98 | 5.88 | 1.2 | 0 | 1.12 | 0.47 | 0.02 | 0.37 | 0.16 |
| -7 | 4.87 | 0.22 | 3.24 | 65.78 | 1.27 | 11.98 | 5.88 | 1.2 | 0 | 1.12 | 0.47 | 0.02 | 0.37 | 0.16 |
| -8 | 4.59 | 0.22 | 3.4 | 70.77 | 0 | 16.71 | 0 | 1.36 | 0 | 1.14 | 0.48 | 0.02 | 0.39 | 0.15 |
| -9 | 4.63 | 0.23 | 3.51 | 60.66 | 2.01 | 8.7 | 7.24 | 0.97 | 0 | 1.18 | 0.52 | 0.02 | 0.3 | 0.11 |
| -10 | 4.58 | 0.19 | 3.66 | 70.68 | 0 | 16.89 | 0 | 1.37 | 0 | 1.22 | 0.54 | 0.02 | 0.22 | 0.03 |
| 5536-3-1 | 4.74 | 0.21 | 3.43 | 87.62 | 1.29 | 10.91 | 7.77 | 1.03 | 0.28 | 1.11 | 0.5 | 0.02 | 0.36 | 0.14 |
| -2 | 4.72 | 0.21 | 3.24 | 67.42 | 1.63 | 10.37 | 8.4 | 0.00 | 0 | 1.12 | 0.49 | 0.02 | 0.36 | 0.15 |
| -3 | 4.24 | 0.21 | 3.52 | 71.31 | 0 | 10.63 | 0 | 1.33 | 0 | 1.12 | 0.46 | 0.02 | 0.4 | 0.14 |
| -4 | 4.64 | 0.21 | 3.45 | 87.92 | 1.66 | 9.07 | 7.97 | 0.91 | 0.33 | 1.14 | 0.47 | 0.02 | 0.37 | 0.14 |
| -5 | 4.81 | 0.26 | 3.31 | 67.19 | 0 | 19.92 | 0.01 | 1.30 | 0 | 1.05 | 0.48 | 0.02 | 0.37 | 0.14 |
| -6 | 4.67 | 0.21 | 3.25 | 67.07 | 1.23 | 11.32 | 8.35 | 0.99 | 0 | 1.16 | 0.47 | 0.02 | 0.33 | 0.16 |
| -7 | 4.63 | 0.10 | 2.94 | 84.8 | 4.34 | 8.45 | 9.95 | 0.03 | 0.44 | 1.13 | 0.37 | 0.01 | 0.27 | 0.12 |
| -8 | 4.68 | 0.22 | 3.68 | 67.33 | 0.71 | 1.2 | 6.94 | 1.1 | 0.24 | 1.18 | 0.48 | 0.03 | 0.36 | 0.17 |

TABLE 5-continued

Fatty Acid Analysis of Seeds from Ma524 Transgenic Brassica Plants

| SPL # | 16:0 % | 16:1 % | 18:0 % | 18:1 | 5,9 18:2 % | 18:2 % | 18:3g % | 18:3 % | 18:4 % | 20:1 % | 22:0 % | 22:1 % | 24:0 % | 24:1 % |
|---|---|---|---|---|---|---|---|---|---|---|---|---|---|---|
| -9 | 4.65 | 0.24 | 3.11 | 67.42 | 0.64 | 12.71 | 8.93 | 1.16 | 0.26 | 1.08 | 0.45 | 0.02 | 0.52 | 0.17 |
| -10 | 4.86 | 0.27 | 3.33 | 55.75 | 0.88 | 12.69 | 7.7 | 1.1 | 0.24 | 1.08 | 0.48 | 0.01 | 0.34 | 0.16 |
| 5536-4-1 | 4.65 | 0.24 | 3.8 | 62.41 | 0 | 84.66 | 0 | 1.8 | 0.01 | 0.00 | 0.46 | 0.02 | 0.33 | 0.13 |
| -2 | 5.37 | 0.31 | 3 | 67.98 | 0.88 | 16.04 | 10.5 | 1.41 | 0 | 0.99 | 0.48 | 0.02 | 0.3 | 0.19 |
| -3 | 4.81 | 0.22 | 3.07 | 63.62 | 0.8 | 16.46 | 7.67 | 1.2 | 0 | 1.18 | 0.45 | 0.02 | 0.29 | 0.14 |
| -4 | 4.39 | 0.19 | 2.93 | 65.97 | 0 | 22.36 | 0 | 1.45 | 0 | 1.17 | 0.41 | 0.03 | 0.32 | 0.15 |
| -5 | 5.22 | 0.29 | 3.85 | 62.1 | 2.35 | 10.25 | 11.39 | 0.93 | 0.41 | 1.04 | 0.8 | 0.02 | 0.47 | 0.17 |
| -6 | 4.66 | 0.18 | 2.85 | 66.79 | 0.5 | 13.03 | 7.00 | 0.97 | 0.22 | 1.28 | 0.42 | 0.02 | 0.31 | 0.14 |
| -7 | 4.85 | 0.28 | 3.03 | 57.43 | 0.26 | 28.04 | 0.01 | 2.59 | 0.01 | 1.13 | 0.56 | 0.02 | 0.4 | 0.23 |
| -8 | 5.42 | 0.28 | 2.94 | 54.8 | 1.84 | 13.79 | 18.87 | 1.38 | 0.53 | 1.7 | 0.55 | 0.02 | 0.35 | 0.19 |
| -9 | 4.88 | 0.24 | 3.32 | 62.3 | 0.56 | 14.86 | 9.04 | 1.34 | 0.29 | 1.13 | 0.52 | 0.02 | 0.37 | 0.19 |
| -10 | 4.53 | 0.2 | 2.73 | 64.2 | 0.07 | 24.15 | 0 | 1.52 | 0 | 1.09 | 0.30 | 0.02 | 0.27 | 0.17 |
| 5536-5-1 | 4.6 | 0.16 | 3.36 | 66.71 | 0.88 | 11.7 | 8.28 | 1.04 | 0.3 | 1.24 | 0.40 | 0.02 | 0.29 | 0.17 |
| -2 | 4.77 | 0.23 | 3.06 | 62.67 | 0.88 | 15.2 | 8.8 | 1.31 | 0.28 | 1.15 | 0.40 | 0.02 | 0.3 | 0.19 |
| -3 | 4.59 | 0.22 | 3.61 | 64.35 | 2.29 | 0.05 | 10.57 | 1.01 | 0.45 | 1.21 | 0.48 | 0.02 | 0.26 | 0.16 |
| -4 | 4.88 | 0.28 | 3.4 | 67.89 | 0.55 | 12.24 | 5.61 | 1.09 | 0.23 | 1.07 | 0.45 | 0.02 | 0.32 | 0.14 |
| -5 | 4.49 | 0.21 | 3.3 | 69.25 | 0.04 | 16.51 | 2.18 | 1.2 | 0 | 1.11 | 0.44 | 0.02 | 0.33 | 0.61 |
| -8 | 4.5 | 0.21 | 3.47 | 70.48 | 0.08 | 14.9 | 2.19 | 1.22 | 0 | 1.13 | 0.49 | 0.02 | 0.33 | 0.16 |
| -7 | 4.39 | 0.21 | 3.44 | 67.59 | 2.38 | 0.24 | 8.98 | 0.80 | 0 | 1.18 | 0.44 | 0.02 | 0.28 | 0.14 |
| -8 | 4.52 | 0.22 | 3.17 | 68.39 | 0.01 | 18.91 | 0.73 | 1.32 | 0.01 | 1.08 | 0.45 | 0.02 | 0.29 | 0.17 |
| -9 | 4.68 | 0.2 | 3.05 | 84.03 | 1.93 | 11.03 | 11.41 | 1.02 | 0.01 | 1.15 | 0.39 | 0.02 | 0.21 | 0.15 |
| -10 | 4.57 | 0.2 | 3.1 | 87.21 | 0.81 | 12.62 | 7.68 | 1.07 | 0.26 | 1.14 | 0.43 | 0.02 | 0.25 | 0.15 |
| 5536-8-1 | 4.95 | 0.26 | 3.14 | 64.04 | 0 | 23.38 | 0 | 1.64 | 0 | 0.99 | 0.42 | 0.02 | 0.38 | 0.17 |
| -2 | 4.01 | 0.26 | 3.71 | 62.93 | 0 | 23.97 | 0 | 1.77 | 0 | 0.95 | 0.53 | 0.02 | 0.42 | 0.19 |
| -3 | 4.73 | 0.25 | 4.04 | 63.83 | 0 | 22.36 | 0.01 | 1.73 | 0 | 1.05 | 0.55 | 0.02 | 0.45 | 0.16 |
| -4 | 6.1 | 0.35 | 3.8 | 60.45 | 0 | 24.45 | 0.01 | 2.13 | 0 | 1.07 | 0.85 | 0.03 | 0.83 | 0.24 |
| -5 | 4.98 | 0.3 | 3.91 | 62.48 | 0 | 23.64 | 0 | 1.77 | 0 | 1.01 | 0.51 | 0.01 | 0.43 | 0.21 |
| -6 | 4.62 | 0.21 | 3.99 | 66.14 | 0 | 20.38 | 0 | 1.48 | 0 | 1.15 | 0.53 | 0.02 | 0.48 | 0.19 |
| -7 | 4.64 | 0.22 | 3.55 | 84.8 | 0 | 22.85 | 0 | 1.38 | 0 | 1.09 | 0.45 | 0.02 | 0.41 | 0.19 |
| -8 | 5.65 | 0.38 | 3.18 | 56.5 | 0 | 30.83 | 0.02 | 0.02 | 0 | 0.98 | 0.56 | 0.03 | 0.39 | 0.28 |
| -9 | 8.53 | 0.63 | 6.0 | 51.76 | 0 | 28.01 | 0 | 0.01 | 0 | 1.41 | 1.21 | 0.07 | 0.90 | 0.33 |
| -10 | 5.52 | 0.4 | 3.07 | 57.92 | 0 | 28.95 | 0 | 0.02 | 0 | 0.96 | 0.62 | 0.02 | 0.41 | 0.16 |
| 5536-10-1 | 4.44 | 0.19 | 3.5 | 88.42 | 0 | 19.51 | 0 | 1.32 | 0 | 1.14 | 0.45 | 0.02 | 0.31 | 0.16 |
| -2 | 4.67 | 0.21 | 3.07 | 66.08 | 0 | 21.99 | 0.01 | 1.36 | 0 | 1.12 | 0.41 | 0.02 | 0.31 | 0.16 |
| -3 | 4.63 | 0.21 | 3.48 | 67.43 | 0 | 20.27 | 0.01 | 1.32 | 0 | 1.12 | 0.46 | 0.02 | 0.21 | 0.08 |
| -4 | 4.69 | 0.19 | 3.22 | 64.68 | 0 | 23.16 | 0 | 1.35 | 0 | 1.08 | 0.40 | 0.02 | 0.38 | 0.2 |
| -5 | 4.58 | 0.2 | 3.4 | 68.75 | 0 | 20.17 | 0.01 | 0.02 | 0 | 1.1 | 0.45 | 0.02 | 0.34 | 0.17 |
| -8 | 4.55 | 0.21 | 0 | 73.56 | 4.08 | 1.91 | 2.76 | 1.21 | 0.07 | 1.24 | 0.51 | 0.02 | 0.19 | 0 |
| -9 | 4.58 | 0.21 | 3.28 | 68.19 | 0 | 21.55 | 0 | 1.35 | 0 | 1.12 | 0.45 | 0.02 | 0.33 | 0.18 |
| -10 | 4.52 | 0.2 | 3.4 | 68.97 | 0 | 19.33 | 0.01 | 1.3 | 0 | 1.13 | 0.46 | 0.02 | 0.35 | 0.10 |

What is claimed is:

1. A nucleic acid construct comprising a nucleotide sequence which encodes a polypeptide comprising the amino acid sequence depicted in SEQ ID NO:6, wherein said nucleotide sequence is operably associated with a transcription or an expression control sequence functional in a plant cell, wherein said nucleotide sequence encodes a functionally active polypeptide which desaturates a fatty acid molecule at carbon 5 from the carboxyl end of said fatty acid molecule.

2. A nucleic acid construct comprising the nucleotide sequence depicted in SEQ ID NO:5, wherein said nucleotide sequence is operably associated with a transcription or an expression control sequence functional in a plant cell, wherein said nucleotide sequence encodes a functionally active polypeptide which desaturates a fatty acid molecule at carbon 5 from the carboxyl end of said fatty acid molecule.

3. A nucleic acid construct comprising a nucleotide sequence which encodes a functionally active desaturase having the amino acid sequence depicted in SEQ ID NO:6, wherein said nucleotide sequence is operably associated with a promoter functional in a plant cell.

4. The nucleic acid construct according to claim 3, wherein said plant cell is a seed cell.

5. The nucleic acid construct according to claim 4, wherein said seed cell is an embryo cell.

6. A microbial or plant host cell comprising at least one copy of a DNA sequence which encodes a functionally active *Mortierella alpina* fatty acid desaturase having the amino acid sequence as depicted in a SEQ NO:6, wherein said cell or parent of said cell was transformed with a vector comprising said DNA sequence, and wherein said DNA sequence is operably associated with an expression control sequence.

7. A method for obtaining altered long chain polyunsaturated fatty acid biosynthesis in a plant, said method comprising:

growing a plant having cells which contain one or more transgenes encoding a transgene expression product which desaturates a fatty acid molecule at carbon 5 from the carboxyl end of said fatty acid molecule, wherein said expression product comprises the amino acid sequence depicted in SEQ ID NO:6 wherein said one or more transgenes is operably associated with an expression control sequence, under conditions whereby said one or more transgenes is expressed, whereby long chain polyunsaturated fatty acid biosynthesis in said cells is altered.

8. The method according to claim 7, wherein said one or more transgenes comprises the nucleotide sequence depicted in SEQ ID NO:5.

9. A nucleic acid construct comprising:

two or more nucleotide sequences depicted in a SEQ ID NO: selected from the group consisting of SEQ ID NO:1, SEQ ID NO:3, and SEQ ID NO:5 linked to a heterologous nucleotide sequence.

10. A nucleic acid construct comprising:

one or more nucleotide sequences depicted in a SEQ ID NO: selected from the group consisting of SEQ ID NO:1, SEQ ID NO:3, and SEQ ID NO:5 operably associated with an expression control sequence functional in a plant cell.

11. The nucleic acid construct according to claim 10, wherein said nucleotide sequence is derived from a fungus.

12. The nucleic acid construct according to claim 11, wherein said fungus is of the genus Mortierella.

13. The nucleic acid construct according to claim 12, wherein said fungus is of the species alpina.

14. The recombinant host cell of claim 6, wherein said host cell is a plant cell.

* * * * *

SEQUENCE LISTING (1) GENERAL INFORMATION:

(iii) NUMBER OF SEQUENCES: 28

(2) INFORMATION FOR SEQ ID NO:1:

(i) SEQUENCE CHARACTERISTICS:
     (A) LENGTH: 1617 base pairs
     (B) TYPE: nucleic acid
     (C) STRANDEDNESS: single
     (D) TOPOLOGY: linear (ii) MOLECULE TYPE: DNA (genomic)

(xi) SEQUENCE DESCRIPTION: SEQ ID NO:1:

```
CGACACTCCT TCCTTCTTCT CACCCGTCCT AGTCCCCTTC AACCCCCCTC TTTGACAAAG      60

ACAACAAACC ATGGCTGCTG CTCCCAGTGT GAGGACGTTT ACTCGGGCCG AGGTTTTGAA     120

TGCCGAGGCT CTGAATGAGG GCAAGAAGGA TGCCGAGGCA CCCTTCTTGA TGATCATCGA     180

CAACAAGGTG TACGATGTCC GCGAGTTCGT CCCTGATCAT CCCGGTGGAA GTGTGATTCT     240
```

```
CACGCACGTT GGCAAGGACG GCACTGACGT CTTTGACACT TTTCACCCCG AGGCTGCTTG      300

GGAGACTCTT GCCAACTTTT ACGTTGGTGA TATTGACGAG AGCGACCGCG ATATCAAGAA      360

TGATGACTTT GCGGCCGAGG TCCGCAAGCT GCGTACCTTG TTCCAGTCTC TTGGTTACTA      420

CGATTCTTCC AAGGCATACT ACGCCTTCAA GGTCTCGTTC AACCTCTGCA TCTGGGGTTT      480

GTCGACGGTC ATTGTGGCCA AGTGGGGCCA GACCTCGACC CTCGCCAACG TGCTCTCGGC      540

TGCGCTTTTG GGTCTGTTCT GGCAGCAGTG CGGATGGTTG GCTCACGACT TTTTGCATCA      600

CCAGGTCTTC CAGGACCGTT TCTGGGGTGA TCTTTTCGGC GCCTTCTTGG GAGGTGTCTG      660

CCAGGGCTTC TCGTCCTCGT GGTGGAAGGA CAAGCACAAC ACTCACCACG CCGCCCCCAA      720

CGTCCACGGC GAGGATCCCG ACATTGACAC CCACCCTCTG TTGACCTGGA GTGAGCATGC      780

GTTGGAGATG TTCTCGGATG TCCCAGATGA GGAGCTGACC CGCATGTGGT CGCGTTTCAT      840

GGTCCTGAAC CAGACCTGGT TTTACTTCCC CATTCTCTCG TTTGCCCGTC TCTCCTGGTG      900

CCTCCAGTCC ATTCTCTTTG TGCTGCCTAA CGGTCAGGCC CACAAGCCCT CGGGCGCGCG      960

TGTGCCCATC TCGTTGGTCG AGCAGCTGTC GCTTGCGATG CACTGGACCT GGTACCTCGC     1020

CACCATGTTC CTGTTCATCA AGGATCCCGT CAACATGCTG GTGTACTTTT TGGTGTCGCA     1080

GGCGGTGTGC GGAAACTTGT TGGCGATCGT GTTCTCGCTC AACCACAACG GTATGCCTGT     1140

GATCTCGAAG GAGGAGGCGG TCGATATGGA TTTCTTCACG AAGCAGATCA TCACGGGTCG     1200

TGATGTCCAC CCGGGTCTAT TTGCCAACTG GTTCACGGGT GGATTGAACT ATCAGATCGA     1260

GCACCACTTG TTCCCTTCGA TGCCTCGCCA CAACTTTTCA AAGATCCAGC TGCTGTCGA     1320

GACCCTGTGC AAAAAGTACA ATGTCCGATA CCACACCACC GGTATGATCG AGGGAACTGC     1380

AGAGGTCTTT AGCCGTCTGA ACGAGGTCTC CAAGGCTGCC TCCAAGATGG GTAAGGCGCA     1440

GTAAAAAAAA AAACAAGGAC GTTTTTTTTC GCCAGTGCCT GTGCCTGTGC CTGCTTCCCT     1500

TGTCAAGTCG AGCGTTTCTG GAAAGGATCG TTCAGTGCAG TATCATCATT CTCCTTTTAC     1560

CCCCCGCTCA TATCTCATTC ATTTCTCTTA TTAAACAACT TGTTCCCCCC TTCACCG       1617

(2) INFORMATION FOR SEQ ID NO:2:

(i) SEQUENCE CHARACTERISTICS:
        (A) LENGTH: 457 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:2:

Met Ala Ala Ala Pro Ser Val Arg Thr Phe Thr Arg Ala Glu Val Leu
1               5                   10                  15

Asn Ala Glu Ala Leu Asn Glu Gly Lys Lys Asp Ala Glu Ala Pro Phe
            20                  25                  30

Leu Met Ile Ile Asp Asn Lys Val Tyr Asp Val Arg Glu Phe Val Pro
        35                  40                  45

Asp His Pro Gly Gly Ser Val Ile Leu Thr His Val Gly Lys Asp Gly
    50                  55                  60

Thr Asp Val Phe Asp Thr Phe His Pro Glu Ala Ala Trp Glu Thr Leu
65                  70                  75                  80

Ala Asn Phe Tyr Val Gly Asp Ile Asp Glu Ser Asp Arg Asp Ile Lys
                85                  90                  95

Asn Asp Asp Phe Ala Ala Glu Val Arg Lys Leu Arg Thr Leu Phe Gln
            100                 105                 110
```

```
Ser Leu Gly Tyr Tyr Asp Ser Ser Lys Ala Tyr Ala Phe Lys Val
        115                 120                 125

Ser Phe Asn Leu Cys Ile Trp Gly Leu Ser Thr Val Ile Val Ala Lys
130                     135                 140

Trp Gly Gln Thr Ser Thr Leu Ala Asn Val Leu Ser Ala Ala Leu Leu
145                 150                 155                 160

Gly Leu Phe Trp Gln Gln Cys Gly Trp Leu Ala His Asp Phe Leu His
                165                 170                 175

His Gln Val Phe Gln Asp Arg Phe Trp Gly Asp Leu Phe Gly Ala Phe
            180                 185                 190

Leu Gly Gly Val Cys Gln Gly Phe Ser Ser Ser Trp Trp Lys Asp Lys
        195                 200                 205

His Asn Thr His His Ala Ala Pro Asn Val His Gly Glu Asp Pro Asp
    210                 215                 220

Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
                245                 250                 255

Met Val Leu Asn Gln Thr Trp Phe Tyr Phe Pro Ile Leu Ser Phe Ala
            260                 265                 270

Arg Leu Ser Trp Cys Leu Gln Ser Ile Leu Phe Val Leu Pro Asn Gly
        275                 280                 285

Gln Ala His Lys Pro Ser Gly Ala Arg Val Pro Ile Ser Leu Val Glu
    290                 295                 300

Gln Leu Ser Leu Ala Met His Trp Thr Trp Tyr Leu Ala Thr Met Phe
305                 310                 315                 320

Leu Phe Ile Lys Asp Pro Val Asn Met Leu Val Tyr Phe Leu Val Ser
                325                 330                 335

Gln Ala Val Cys Gly Asn Leu Leu Ala Ile Val Phe Ser Leu Asn His
            340                 345                 350

Asn Gly Met Pro Val Ile Ser Lys Glu Glu Ala Val Asp Met Asp Phe
        355                 360                 365

Phe Thr Lys Gln Ile Ile Thr Gly Arg Asp Val His Pro Gly Leu Phe
    370                 375                 380

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
                405                 410                 415

Glu Thr Leu Cys Lys Lys Tyr Asn Val Arg Tyr His Thr Thr Gly Met
            420                 425                 430

Ile Glu Gly Thr Ala Glu Val Phe Ser Arg Leu Asn Glu Val Ser Lys
        435                 440                 445

Ala Ala Ser Lys Met Gly Lys Ala Gln
    450                 455

(2) INFORMATION FOR SEQ ID NO:3:

(i) SEQUENCE CHARACTERISTICS:
        (A) LENGTH: 1488 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:
```

```
GTCCCCTGTC GCTGTCGGCA CACCCCATCC TCCCTCGCTC CCTCTGCGTT TGTCCTTGGC      60

CCACCGTCTC TCCTCCACCC TCCGAGACGA CTGCAACTGT AATCAGGAAC CGACAAATAC     120

ACGATTTCTT TTTACTCAGC ACCAACTCAA AATCCTCAAC CGCAACCCTT TTTCAGGATG     180

GCACCTCCCA ACACTATCGA TGCCGGTTTG ACCCAGCGTC ATATCAGCAC CTCGGCCCCA     240

AACTCGGCCA AGCCTGCCTT CGAGCGCAAC TACCAGCTCC CCGAGTTCAC CATCAAGGAG     300

ATCCGAGAGT GCATCCCTGC CCACTGCTTT GAGCGCTCCG GTCTCCGTGG TCTCTGCCAC     360

GTTGCCATCG ATCTGACTTG GGCGTCGCTC TTGTTCCTGG CTGCGACCCA GATCGACAAG     420

TTTGAGAATC CCTTGATCCG CTATTTGGCC TGGCCTGTTT ACTGGATCAT GCAGGGTATT     480

GTCTGCACCG GTGTCTGGGT GCTGGCTCAC GAGTGTGGTC ATCAGTCCTT CTCGACCTCC     540

AAGACCCTCA ACAACACAGT TGGTTGGATC TTGCACTCGA TGCTCTTGGT CCCCTACCAC     600

TCCTGGAGAA TCTCGCACTC GAAGCACCAC AAGGCCACTG GCCATATGAC CAAGGACCAG     660

GTCTTTGTGC CCAAGACCCG CTCCCAGGTT GGCTTGCCTC CCAAGGAGAA CGCTGCTGCT     720

GCCGTTCAGG AGGAGGACAT GTCCGTGCAC CTGGATGAGG AGGCTCCCAT TGTGACTTTG     780

TTCTGGATGG TGATCCAGTT CTTGTTCGGA TGGCCCGCGT ACCTGATTAT GAACGCCTCT     840

GGCCAAGACT ACGGCCGCTG GACCTCGCAC TTCCACACGT ACTCGCCCAT CTTTGAGCCC     900

CGCAACTTTT TCGACATTAT TATCTCGGAC CTCGGTGTGT TGGCTGCCCT CGGTGCCCTG     960

ATCTATGCCT CCATGCAGTT GTCGCTCTTG ACCGTCACCA AGTACTATAT TGTCCCCTAC    1020

CTCTTTGTCA ACTTTTGGTT GGTCCTGATC ACCTTCTTGC AGCACACCGA TCCCAAGCTG    1080

CCCCATTACC GCGAGGGTGC CTGGAATTTC AGCGTGGAG CTCTTTGCAC CGTTGACCGC    1140

TCGTTTGGCA AGTTCTTGGA CCATATGTTC CACGGCATTG TCCACACCCA TGTGGCCCAT    1200

CACTTGTTCT CGCAAATGCC GTTCTACCAT GCTGAGGAAG CTACCTATCA TCTCAAGAAA    1260

CTGCTGGGAG AGTACTATGT GTACGACCCA TCCCCGATCG TCGTTGCGGT CTGGAGGTCG    1320

TTCCGTGAGT GCCGATTCGT GGAGGATCAG GGAGACGTGG TCTTTTTCAA GAAGTAAAAA    1380

AAAAGACAAT GGACCACACA CAACCTTGTC TCTACAGACC TACGTATCAT GTAGCCATAC    1440

CACTTCATAA AGAACATGA GCTCTAGAGG CGTGTCATTC GCGCCTCC                 1488

(2) INFORMATION FOR SEQ ID NO:4:

(i) SEQUENCE CHARACTERISTICS:
        (A) LENGTH: 399 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:4:

Met Ala Pro Pro Asn Thr Ile Asp Ala Gly Leu Thr Gln Arg His Ile
1               5                   10                  15

Ser Thr Ser Ala Pro Asn Ser Ala Lys Pro Ala Phe Glu Arg Asn Tyr
            20                  25                  30

Gln Leu Pro Glu Phe Thr Ile Lys Glu Ile Arg Glu Cys Ile Pro Ala
        35                  40                  45

His Cys Phe Glu Arg Ser Gly Leu Arg Gly Leu Cys His Val Ala Ile
    50                  55                  60

Asp Leu Thr Trp Ala Ser Leu Leu Phe Leu Ala Ala Thr Gln Ile Asp
65                  70                  75                  80
```

```
Lys Phe Glu Asn Pro Leu Ile Arg Tyr Leu Ala Trp Pro Val Tyr Trp
                 85                  90                  95
Ile Met Gln Gly Ile Val Cys Thr Gly Val Trp Val Leu Ala His Glu
            100                 105                 110
Cys Gly His Gln Ser Phe Ser Thr Ser Lys Thr Leu Asn Asn Thr Val
            115                 120             125
Gly Trp Ile Leu His Ser Met Leu Leu Val Pro Tyr His Ser Trp Arg
        130                 135                 140
Ile Ser His Ser Lys His His Lys Ala Thr Gly His Met Thr Lys Asp
145                 150                 155                 160
Gln Val Phe Val Pro Lys Thr Arg Ser Gln Val Gly Leu Pro Pro Lys
                165                 170                 175
Glu Asn Ala Ala Ala Val Gln Glu Asp Met Ser Val His Leu
                180                 185                 190
Asp Glu Glu Ala Pro Ile Val Thr Leu Phe Trp Met Val Ile Gln Phe
            195                 200                 205
Leu Phe Gly Trp Pro Ala Tyr Leu Ile Met Asn Ala Ser Gly Gln Asp
        210                 215                 220
Tyr Gly Arg Trp Thr Ser His Phe His Thr Tyr Ser Pro Ile Phe Glu
225                 230                 235                 240
Pro Arg Asn Phe Phe Asp Ile Ile Ile Ser Asp Leu Gly Val Leu Ala
                245                 250                 255
Ala Leu Gly Ala Leu Ile Tyr Ala Ser Met Gln Leu Ser Leu Leu Thr
            260                 265                 270
Val Thr Lys Tyr Tyr Ile Val Pro Tyr Leu Phe Val Asn Phe Trp Leu
            275                 280                 285
Val Leu Ile Thr Phe Leu Gln His Thr Asp Pro Lys Leu Pro His Tyr
        290                 295                 300
Arg Glu Gly Ala Trp Asn Phe Gln Arg Gly Ala Leu Cys Thr Val Asp
305                 310                 315                 320
Arg Ser Phe Gly Lys Phe Leu Asp His Met Phe His Gly Ile Val His
                325                 330                 335
Thr His Val Ala His His Leu Phe Ser Gln Met Pro Phe Tyr His Ala
            340                 345                 350
Glu Glu Ala Thr Tyr His Leu Lys Lys Leu Leu Gly Glu Tyr Tyr Val
            355                 360                 365
Tyr Asp Pro Ser Pro Ile Val Val Ala Val Trp Arg Ser Phe Arg Glu
        370                 375                 380
Cys Arg Phe Val Glu Asp Gln Gly Asp Val Val Phe Phe Lys Lys
385                 390                 395

(2) INFORMATION FOR SEQ ID NO:5:

(i) SEQUENCE CHARACTERISTICS:
        (A) LENGTH: 1483 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GCTTCCTCCA GTTCATCCTC CATTTCGCCA CCTGCATTCT TTACGACCGT TAAGCAAGAT      60

GGGAACGGAC CAAGGAAAAA CCTTCACCTG GAAGAGCTG GCGGCCCATA ACACCAAGGA      120

CGACCTACTC TTGGCCATCC GCGGCAGGGT GTACGATGTC ACAAAGTTCT TGAGCCGCCA    180
```

-continued

```
TCCTGGTGGA GTGGACACTC TCCTGCTCGG AGCTGGCCGA GATGTTACTC CGGTCTTTGA    240

GATGTATCAC GCGTTTGGGG CTGCAGATGC CATTATGAAG AAGTACTATG TCGGTACACT    300

GGTCTCGAAT GAGCTGCCCA TCTTCCCGGA GCCAACGGTG TTCCACAAAA CCATCAAGAC    360

GAGAGTCGAG GGCTACTTTA CGGATCGGAA CATTGATCCC AAGAATAGAC CAGAGATCTG    420

GGGACGATAC GCTCTTATCT TTGGATCCTT GATCGCTTCC TACTACGCGC AGCTCTTTGT    480

GCCTTTCGTT GTCGAACGCA CATGGCTTCA GGTGGTGTTT GCAATCATCA TGGGATTTGC    540

GTGCGCACAA GTCGGACTCA ACCCTCTTCA TGATGCGTCT CACTTTTCAG TGACCCACAA    600

CCCCACTGTC TGGAAGATTC TGGGAGCCAC GCACGACTTT TTCAACGGAG CATCGTACCT    660

GGTGTGGATG TACCAACATA TGCTCGGCCA TCACCCCTAC ACCAACATTG CTGGAGCAGA    720

TCCCGACGTG TCGACGTCTG AGCCCGATGT TCGTCGTATC AAGCCCAACC AAAAGTGGTT    780

TGTCAACCAC ATCAACCAGC ACATGTTTGT TCCTTTCCTG TACGGACTGC TGGCGTTCAA    840

GGTGCGCATT CAGGACATCA ACATTTTGTA CTTTGTCAAG ACCAATGACG CTATTCGTGT    900

CAATCCCATC TCGACATGGC ACACTGTGAT GTTCTGGGGC GGCAAGGCTT TCTTTGTCTG    960

GTATCGCCTG ATTGTTCCCC TGCAGTATCT GCCCCTGGGC AAGGTGCTGC TCTTGTTCAC    1020

GGTCGCGGAC ATGGTGTCGT CTTACTGGCT GGCGCTGACC TTCCAGGCGA ACCACGTTGT    1080

TGAGGAAGTT CAGTGGCCGT TGCCTGACGA GAACGGGATC ATCCAAAAGG ACTGGGCAGC    1140

TATGCAGGTC GAGACTACGC AGGATTACGC ACACGATTCG CACCTCTGGA CCAGCATCAC    1200

TGGCAGCTTG AACTACCAGG CTGTGCACCA TCTGTTCCCC AACGTGTCGC AGCACCATTA    1260

TCCCGATATT CTGGCCATCA TCAAGAACAC CTGCAGCGAG TACAAGGTTC ATACCTTGT    1320

CAAGGATACG TTTTGGCAAG CATTTGCTTC ACATTTGGAG CACTTGCGTG TTCTTGGACT    1380

CCGTCCCAAG GAAGAGTAGA AGAAAAAAAG CGCCGAATGA AGTATTGCCC CCTTTTTCTC    1440

CAAGAATGGC AAAAGGAGAT CAAGTGGACA TTCTCTATGA AGA                     1483
```

(2) INFORMATION FOR SEQ ID NO:6:

(i) SEQUENCE CHARACTERISTICS:
        (A) LENGTH: 446 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:6:

```
Met Gly Thr Asp Gln Gly Lys Thr Phe Thr Trp Glu Glu Leu Ala Ala
1               5                   10                  15

His Asn Thr Lys Asp Asp Leu Leu Leu Ala Ile Arg Gly Arg Val Tyr
            20                  25                  30

Asp Val Thr Lys Phe Leu Ser Arg His Pro Gly Val Asp Thr Leu
        35                  40                  45

Leu Leu Gly Ala Gly Arg Asp Val Thr Pro Val Phe Glu Met Tyr His
    50                  55                  60

Ala Phe Gly Ala Ala Asp Ala Ile Met Lys Lys Tyr Tyr Val Gly Thr
65                  70                  75                  80

Leu Val Ser Asn Glu Leu Pro Ile Phe Pro Glu Pro Thr Val Phe His
                85                  90                  95

Lys Thr Ile Lys Thr Arg Val Glu Gly Tyr Phe Thr Asp Arg Asn Ile
                100                 105                 110

Asp Pro Lys Asn Arg Pro Glu Ile Trp Gly Arg Tyr Ala Leu Ile Phe
```

-continued

```
            115                 120                 125
Gly Ser Leu Ile Ala Ser Tyr Tyr Ala Gln Leu Phe Val Pro Phe Val
        130                 135                 140

Val Glu Arg Thr Trp Leu Gln Val Val Phe Ala Ile Ile Met Gly Phe
145                 150                 155                 160

Ala Cys Ala Gln Val Gly Leu Asn Pro Leu His Asp Ala Ser His Phe
                165                 170                 175

Ser Val Thr His Asn Pro Thr Val Trp Lys Ile Leu Gly Ala Thr His
            180                 185                 190

Asp Phe Phe Asn Gly Ala Ser Tyr Leu Val Trp Met Tyr Gln His Met
        195                 200                 205

Leu Gly His His Pro Tyr Thr Asn Ile Ala Gly Ala Asp Pro Asp Val
    210                 215                 220

Ser Thr Ser Glu Pro Asp Val Arg Arg Ile Lys Pro Asn Gln Lys Trp
225                 230                 235                 240

Phe Val Asn His Ile Asn Gln His Met Phe Val Pro Phe Leu Tyr Gly
                245                 250                 255

Leu Leu Ala Phe Lys Val Arg Ile Gln Asp Ile Asn Ile Leu Tyr Phe
            260                 265                 270

Val Lys Thr Asn Asp Ala Ile Arg Val Asn Pro Ile Ser Thr Trp His
        275                 280                 285

Thr Val Met Phe Trp Gly Gly Lys Ala Phe Phe Val Trp Tyr Arg Leu
    290                 295                 300

Ile Val Pro Leu Gln Tyr Leu Pro Leu Gly Lys Val Leu Leu Leu Phe
305                 310                 315                 320

Thr Val Ala Asp Met Val Ser Ser Tyr Trp Leu Ala Leu Thr Phe Gln
                325                 330                 335

Ala Asn His Val Val Glu Glu Val Gln Trp Pro Leu Pro Asp Glu Asn
            340                 345                 350

Gly Ile Ile Gln Lys Asp Trp Ala Ala Met Gln Val Glu Thr Thr Gln
        355                 360                 365

Asp Tyr Ala His Asp Ser His Leu Trp Thr Ser Ile Thr Gly Ser Leu
    370                 375                 380

Asn Tyr Gln Ala Val His His Leu Phe Pro Asn Val Ser Gln His His
385                 390                 395                 400

Tyr Pro Asp Ile Leu Ala Ile Ile Lys Asn Thr Cys Ser Glu Tyr Lys
                405                 410                 415

Val Pro Tyr Leu Val Lys Asp Thr Phe Trp Gln Ala Phe Ala Ser His
            420                 425                 430

Leu Glu His Leu Arg Val Leu Gly Leu Arg Pro Lys Glu Glu
        435                 440                 445

(2) INFORMATION FOR SEQ ID NO:7:

(i) SEQUENCE CHARACTERISTICS:
        (A) LENGTH: 355 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:7:

Glu Val Arg Lys Leu Arg Thr Leu Phe Gln Ser Leu Gly Tyr Tyr Asp
1               5                   10                  15

Ser Ser Lys Ala Tyr Tyr Ala Phe Lys Val Ser Phe Asn Leu Cys Ile
```

-continued

```
            20                  25                  30
Trp Gly Leu Ser Thr Val Ile Val Ala Lys Trp Gly Gln Thr Ser Thr
            35                  40                  45
Leu Ala Asn Val Leu Ser Ala Leu Leu Gly Leu Phe Trp Gln Gln
 50                  55                  60
Cys Gly Trp Leu Ala His Asp Phe Leu His Gln Val Phe Gln Asp
 65                  70                  75                  80
Arg Phe Trp Gly Asp Leu Phe Gly Ala Phe Leu Gly Gly Val Cys Gln
                85                  90                  95
Gly Phe Ser Ser Ser Trp Trp Lys Asp Lys His Asn Thr His His Ala
                100                 105                 110
Ala Pro Asn Val His Gly Glu Asp Pro Asp Ile Asp Thr His Pro Leu
                115                 120                 125
Leu Thr Trp Ser Glu His Ala Leu Glu Met Phe Ser Asp Val Pro Asp
 130                 135                 140
Glu Glu Leu Thr Arg Met Trp Ser Arg Phe Met Val Leu Asn Gln Thr
 145                 150                 155                 160
Trp Phe Tyr Phe Pro Ile Leu Ser Phe Ala Arg Leu Ser Trp Cys Leu
                165                 170                 175
Gln Ser Ile Leu Phe Val Leu Pro Asn Gly Gln Ala His Lys Pro Ser
                180                 185                 190
Gly Ala Arg Val Pro Ile Ser Leu Val Glu Gln Leu Ser Leu Ala Met
                195                 200                 205
His Trp Thr Trp Tyr Leu Ala Thr Met Phe Leu Phe Ile Lys Asp Pro
                210                 215                 220
Val Asn Met Leu Val Tyr Phe Leu Val Ser Gln Ala Val Cys Gly Asn
 225                 230                 235                 240
Leu Leu Ala Ile Val Phe Ser Leu Asn His Asn Gly Met Pro Val Ile
                245                 250                 255
Ser Lys Glu Glu Ala Val Asp Met Asp Phe Phe Thr Lys Gln Ile Ile
                260                 265                 270
Thr Gly Arg Asp Val His Pro Gly Leu Phe Ala Asn Trp Phe Thr Gly
                275                 280                 285
Gly Leu Asn Tyr Gln Ile Glu His His Leu Phe Pro Ser Met Pro Arg
                290                 295                 300
His Asn Phe Ser Lys Ile Gln Pro Ala Val Glu Thr Leu Cys Lys Lys
 305                 310                 315                 320
Tyr Asn Val Arg Tyr His Thr Thr Gly Met Ile Glu Gly Thr Ala Glu
                325                 330                 335
Val Phe Ser Arg Leu Asn Glu Val Ser Lys Ala Ala Ser Lys Met Gly
                340                 345                 350
Lys Ala Gln
            355
```

(2) INFORMATION FOR SEQ ID NO:8:

(i) SEQUENCE CHARACTERISTICS:
        (A) LENGTH: 104 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:8:

Val Thr Leu Tyr Thr Leu Ala Phe Val Ala Ala Asn Ser Leu Gly Val

```
  1               5                   10                  15
Leu Tyr Gly Val Leu Ala Cys Pro Ser Val Xaa Pro His Gln Ile Ala
                20                  25                  30
Ala Gly Leu Leu Gly Leu Leu Trp Ile Gln Ser Ala Tyr Ile Gly Xaa
            35                  40                  45
Asp Ser Gly His Tyr Val Ile Met Ser Asn Lys Ser Asn Asn Xaa Phe
        50                  55                  60
Ala Gln Leu Leu Ser Gly Asn Cys Leu Thr Gly Ile Ile Ala Trp Trp
65                  70                  75                  80
Lys Trp Thr His Asn Ala His His Leu Ala Cys Asn Ser Leu Asp Tyr
                85                  90                  95
Gly Pro Asn Leu Gln His Ile Pro
                100
```

(2) INFORMATION FOR SEQ ID NO:9:

(i) SEQUENCE CHARACTERISTICS:
        (A) LENGTH: 252 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:9:

```
Gly Val Leu Tyr Gly Val Leu Ala Cys Thr Ser Val Phe Ala His Gln
1               5                   10                  15
Ile Ala Ala Ala Leu Leu Gly Leu Leu Trp Ile Gln Ser Ala Tyr Ile
                20                  25                  30
Gly His Asp Ser Gly His Tyr Val Ile Met Ser Asn Lys Ser Tyr Asn
            35                  40                  45
Arg Phe Ala Gln Leu Leu Ser Gly Asn Cys Leu Thr Gly Ile Ser Ile
        50                  55                  60
Ala Trp Trp Lys Trp Thr His Asn Ala His His Leu Ala Cys Asn Ser
65                  70                  75                  80
Leu Asp Tyr Asp Pro Asp Leu Gln His Ile Pro Val Phe Ala Val Ser
                85                  90                  95
Thr Lys Phe Phe Ser Ser Leu Thr Ser Arg Phe Tyr Asp Arg Lys Leu
                100                 105                 110
Thr Phe Gly Pro Val Ala Arg Phe Leu Val Ser Tyr Gln His Phe Thr
            115                 120                 125
Tyr Tyr Pro Val Asn Cys Phe Gly Arg Ile Asn Leu Phe Ile Gln Thr
        130                 135                 140
Phe Leu Leu Leu Phe Ser Lys Arg Glu Val Pro Asp Arg Ala Leu Asn
145                 150                 155                 160
Phe Ala Gly Ile Leu Val Phe Trp Thr Trp Phe Pro Leu Leu Val Ser
                165                 170                 175
Cys Leu Pro Asn Trp Pro Glu Arg Phe Phe Val Phe Thr Ser Phe
                180                 185                 190
Thr Val Thr Ala Leu Gln His Ile Gln Phe Thr Leu Asn His Phe Ala
            195                 200                 205
Ala Asp Val Tyr Val Gly Pro Pro Thr Gly Ser Asp Trp Phe Glu Lys
        210                 215                 220
Gln Ala Ala Gly Thr Ile Asp Ile Ser Cys Arg Ser Tyr Met Asp Trp
225                 230                 235                 240
Phe Phe Gly Gly Leu Gln Phe Gln Leu Glu His His
```

245            250

(2) INFORMATION FOR SEQ ID NO:10:

(i) SEQUENCE CHARACTERISTICS:
       (A) LENGTH: 125 amino acids
       (B) TYPE: amino acid
       (C) STRANDEDNESS: Not Relevant
       (D) TOPOLOGY: linear (ii) MOLECULE TYPE: peptide (xi) SEQUENCE DESCRIPTION: SEQ ID NO:10:

Gly Xaa Xaa Asn Phe Ala Gly Ile Leu Val Phe Trp Thr Trp Phe Pro
1               5                  10                  15

Leu Leu Val Ser Cys Leu Pro Asn Trp Pro Glu Arg Phe Xaa Phe Val
            20                  25                  30

Phe Thr Gly Phe Thr Val Thr Ala Leu Gln His Ile Gln Phe Thr Leu
        35                  40                  45

Asn His Phe Ala Ala Asp Val Tyr Val Gly Pro Pro Thr Gly Ser Asp
    50                  55                  60

Trp Phe Glu Lys Gln Ala Ala Gly Thr Ile Asp Ile Ser Cys Arg Ser
65                  70                  75                  80

Tyr Met Asp Trp Phe Phe Cys Gly Leu Gln Phe Gln Leu Glu His His
                85                  90                  95

Leu Phe Pro Arg Leu Pro Arg Cys His Leu Arg Lys Val Ser Pro Val
            100                 105                 110

Gly Gln Arg Gly Phe Gln Arg Lys Xaa Asn Leu Ser Xaa
            115                 120                 125

(2) INFORMATION FOR SEQ ID NO:11:

(i) SEQUENCE CHARACTERISTICS:
       (A) LENGTH: 131 amino acids
       (B) TYPE: amino acid
       (C) STRANDEDNESS: Not Relevant
       (D) TOPOLOGY: linear (ii) MOLECULE TYPE: peptide (xi) SEQUENCE DESCRIPTION: SEQ ID NO:11:

Pro Ala Thr Glu Val Gly Gly Leu Ala Trp Met Ile Thr Phe Tyr Val
1               5                  10                  15

Arg Phe Phe Leu Thr Tyr Val Pro Leu Leu Gly Leu Lys Ala Phe Leu
            20                  25                  30

Gly Leu Phe Phe Ile Val Arg Phe Leu Glu Ser Asn Trp Phe Val Trp
        35                  40                  45

Val Thr Gln Met Asn His Ile Pro Met His Ile Asp His Asp Arg Asn
    50                  55                  60

Met Asp Trp Val Ser Thr Gln Leu Gln Ala Thr Cys Asn Val His Lys
65                  70                  75                  80

Ser Ala Phe Asn Asp Trp Phe Ser Gly His Leu Asn Phe Gln Ile Glu
                85                  90                  95

His His Leu Phe Pro Thr Met Pro Arg His Asn Tyr His Xaa Val Ala
            100                 105                 110

Pro Leu Val Gln Ser Leu Cys Ala Lys His Gly Ile Glu Tyr Gln Ser
            115                 120                 125

Lys Pro Leu
    130

(2) INFORMATION FOR SEQ ID NO:12:

(i) SEQUENCE CHARACTERISTICS:
        (A) LENGTH: 87 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:12:

```
Cys Ser Pro Lys Ser Ser Pro Thr Arg Asn Met Thr Pro Ser Pro Phe
1               5                   10                  15

Ile Asp Trp Leu Trp Gly Gly Leu Asn Tyr Gln Ile Glu His His Leu
            20                  25                  30

Phe Pro Thr Met Pro Arg Cys Asn Leu Asn Arg Cys Met Lys Tyr Val
            35                  40                  45

Lys Glu Trp Cys Ala Glu Asn Asn Leu Pro Tyr Leu Val Asp Asp Tyr
50                  55                  60

Phe Val Gly Tyr Asn Leu Asn Leu Gln Gln Leu Lys Asn Met Ala Glu
65                  70                  75                  80

Leu Val Gln Ala Lys Ala Ala
                85
```

(2) INFORMATION FOR SEQ ID NO:13:

(i) SEQUENCE CHARACTERISTICS:
        (A) LENGTH: 143 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:13:

```
Arg His Glu Ala Ala Arg Gly Gly Thr Arg Leu Ala Tyr Met Leu Val
1               5                   10                  15

Cys Met Gln Trp Thr Asp Leu Leu Trp Ala Ala Ser Phe Tyr Ser Arg
            20                  25                  30

Phe Phe Leu Ser Tyr Ser Pro Phe Tyr Gly Ala Thr Gly Thr Leu Leu
            35                  40                  45

Leu Phe Val Ala Val Arg Val Leu Glu Ser His Trp Phe Val Trp Ile
50                  55                  60

Thr Gln Met Asn His Ile Pro Lys Glu Ile Gly His Glu Lys His Arg
65                  70                  75                  80

Asp Trp Ala Ser Ser Gln Leu Ala Ala Thr Cys Asn Val Glu Pro Ser
                85                  90                  95

Leu Phe Ile Asp Trp Phe Ser Gly His Leu Asn Phe Gln Ile Glu His
            100                 105                 110

His Leu Phe Pro Thr Met Thr Arg His Asn Tyr Arg Xaa Val Ala Pro
            115                 120                 125

Leu Val Lys Ala Phe Cys Ala Lys His Gly Leu His Tyr Glu Val
            130                 135                 140
```

(2) INFORMATION FOR SEQ ID NO:14:

(i) SEQUENCE CHARACTERISTICS:
        (A) LENGTH: 186 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:14:

```
Leu His His Thr Tyr Thr Asn Ile Ala Gly Ala Asp Pro Asp Val Ser
1               5                   10                  15

Thr Ser Glu Pro Asp Val Arg Arg Ile Lys Pro Asn Gln Lys Trp Phe
            20                  25                  30

Val Asn His Ile Asn Gln His Met Phe Val Pro Phe Leu Tyr Gly Leu
                35                  40                  45

Leu Ala Phe Lys Val Arg Ile Gln Asp Ile Asn Ile Leu Tyr Phe Val
        50                  55                  60

Lys Thr Asn Asp Ala Ile Arg Val Asn Pro Ile Ser Thr Trp His Thr
65                  70                  75                  80

Val Met Phe Trp Gly Gly Lys Ala Phe Phe Val Trp Tyr Arg Leu Ile
                85                  90                  95

Val Pro Leu Gln Tyr Leu Pro Leu Gly Lys Val Leu Leu Leu Phe Thr
            100                 105                 110

Val Ala Asp Met Val Ser Ser Tyr Trp Leu Ala Leu Thr Phe Gln Ala
                115                 120                 125

Asn Tyr Val Val Glu Glu Val Gln Trp Pro Leu Pro Asp Glu Asn Gly
130                 135                 140

Ile Ile Gln Lys Asp Trp Ala Ala Met Gln Val Glu Thr Thr Gln Asp
145                 150                 155                 160

Tyr Ala His Asp Ser His Leu Trp Thr Ser Ile Thr Gly Ser Leu Asn
                165                 170                 175

Tyr Gln Xaa Val His His Leu Phe Pro His
            180                 185
```

(2) INFORMATION FOR SEQ ID NO:15:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:15:

```
His Xaa Xaa His His
1               5
```

(2) INFORMATION FOR SEQ ID NO:16:

(i) SEQUENCE CHARACTERISTICS:
        (A) LENGTH: 446 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:16:

```
Met Ala Ala Gln Ile Lys Lys Tyr Ile Thr Ser Asp Glu Leu Lys Asn
1               5                   10                  15

His Asp Lys Pro Gly Asp Leu Trp Ile Ser Ile Gln Gly Lys Ala Tyr
            20                  25                  30

Asp Val Ser Asp Trp Val Lys Asp His Pro Gly Gly Ser Phe Pro Leu
                35                  40                  45
```

Lys Ser Leu Ala Gly Gln Glu Val Thr Asp Ala Phe Val Ala Phe His
50              55                  60

Pro Ala Ser Thr Trp Lys Asn Leu Asp Lys Phe Phe Thr Gly Tyr Tyr
65              70                  75                  80

Leu Lys Asp Tyr Ser Val Ser Glu Val Ser Lys Val Tyr Arg Lys Leu
                85                  90                  95

Val Phe Glu Phe Ser Lys Met Gly Leu Tyr Asp Lys Lys Gly His Ile
            100                 105                 110

Met Phe Ala Thr Leu Cys Phe Ile Ala Met Leu Phe Ala Met Ser Val
                115                 120                 125

Tyr Gly Val Leu Phe Cys Glu Gly Val Leu Val His Leu Phe Ser Gly
        130                 135                 140

Cys Leu Met Gly Phe Leu Trp Ile Gln Ser Gly Trp Ile Gly His Asp
145                 150                 155                 160

Ala Gly His Tyr Met Val Val Ser Asp Ser Arg Leu Asn Lys Phe Met
                165                 170                 175

Gly Ile Phe Ala Ala Asn Cys Leu Ser Gly Ile Ser Ile Gly Trp Trp
            180                 185                 190

Lys Trp Asn His Asn Ala His His Ile Ala Cys Asn Ser Leu Glu Tyr
                195                 200                 205

Asp Pro Asp Leu Gln Tyr Ile Pro Phe Leu Val Val Ser Ser Lys Phe
210                 215                 220

Phe Gly Ser Leu Thr Ser His Phe Tyr Glu Lys Arg Leu Thr Phe Asp
225                 230                 235                 240

Ser Leu Ser Arg Phe Phe Val Ser Tyr Gln His Trp Thr Phe Tyr Pro
                245                 250                 255

Ile Met Cys Ala Ala Arg Leu Asn Met Tyr Val Gln Ser Leu Ile Met
                260                 265                 270

Leu Leu Thr Lys Arg Asn Val Ser Tyr Arg Ala Gln Glu Leu Leu Gly
            275                 280                 285

Cys Leu Val Phe Ser Ile Trp Tyr Pro Leu Leu Val Ser Cys Leu Pro
290                 295                 300

Asn Trp Gly Glu Arg Ile Met Phe Val Ile Ala Ser Leu Ser Val Thr
305                 310                 315                 320

Gly Met Gln Gln Val Gln Phe Ser Leu Asn His Phe Ser Ser Ser Val
                325                 330                 335

Tyr Val Gly Lys Pro Lys Gly Asn Asn Trp Phe Glu Lys Gln Thr Asp
            340                 345                 350

Gly Thr Leu Asp Ile Ser Cys Pro Pro Trp Met Asp Trp Phe His Gly
        355                 360                 365

Gly Leu Gln Phe Gln Ile Glu His His Leu Phe Pro Lys Met Pro Arg
    370                 375                 380

Cys Asn Leu Arg Lys Ile Ser Pro Tyr Val Ile Glu Leu Cys Lys Lys
385                 390                 395                 400

His Asn Leu Pro Tyr Asn Tyr Ala Ser Phe Ser Lys Ala Asn Glu Met
                405                 410                 415

Thr Leu Arg Thr Leu Arg Asn Thr Ala Leu Gln Ala Arg Asp Ile Thr
            420                 425                 430

Lys Pro Leu Pro Lys Asn Leu Val Trp Glu Ala Leu His Thr
435                 440                 445

(2) INFORMATION FOR SEQ ID NO:17:

(i) SEQUENCE CHARACTERISTICS:

-continued

```
    (A) LENGTH: 359 amino acids
    (B) TYPE: amino acid
    (C) STRANDEDNESS: Not Relevant
    (D) TOPOLOGY: linear (ii) MOLECULE TYPE: peptide (xi) SEQUENCE DESCRIPTION: SEQ ID NO:17:

Met Leu Thr Ala Glu Arg Ile Lys Phe Thr Gln Lys Arg Gly Phe Arg
1               5                   10                  15

Arg Val Leu Asn Gln Arg Val Asp Ala Tyr Phe Ala Glu His Gly Leu
                20                  25                  30

Thr Gln Arg Asp Asn Pro Ser Met Tyr Leu Lys Thr Leu Ile Ile Val
            35                  40                  45

Leu Trp Leu Phe Ser Ala Trp Ala Phe Val Leu Phe Ala Pro Val Ile
    50                  55                  60

Phe Pro Val Arg Leu Leu Gly Cys Met Val Leu Ala Ile Ala Leu Ala
65                  70                  75                  80

Ala Phe Ser Phe Asn Val Gly His Asp Ala Asn His Asn Ala Tyr Ser
                85                  90                  95

Ser Asn Pro His Ile Asn Arg Val Leu Gly Met Thr Tyr Asp Phe Val
                100                 105                 110

Gly Leu Ser Ser Phe Leu Trp Arg Tyr Arg His Asn Tyr Leu His His
                115                 120                 125

Thr Tyr Thr Asn Ile Leu Gly His Asp Val Glu Ile His Gly Asp Gly
        130                 135                 140

Ala Val Arg Met Ser Pro Glu Gln Glu His Val Gly Ile Tyr Arg Phe
145                 150                 155                 160

Gln Gln Phe Tyr Ile Trp Gly Leu Tyr Leu Phe Ile Pro Phe Tyr Trp
                165                 170                 175

Phe Leu Tyr Asp Val Tyr Leu Val Leu Asn Lys Gly Lys Tyr His Asp
                180                 185                 190

His Lys Ile Pro Pro Phe Gln Pro Leu Glu Leu Ala Ser Leu Leu Gly
        195                 200                 205

Ile Lys Leu Leu Trp Leu Gly Tyr Val Phe Gly Leu Pro Leu Ala Leu
        210                 215                 220

Gly Phe Ser Ile Pro Glu Val Leu Ile Gly Ala Ser Val Thr Tyr Met
225                 230                 235                 240

Thr Tyr Gly Ile Val Val Cys Thr Ile Phe Met Leu Ala His Val Leu
                245                 250                 255

Glu Ser Thr Glu Phe Leu Thr Pro Asp Gly Glu Ser Gly Ala Ile Asp
                260                 265                 270

Asp Glu Trp Ala Ile Cys Gln Ile Arg Thr Thr Ala Asn Phe Ala Thr
        275                 280                 285

Asn Asn Pro Phe Trp Asn Trp Phe Cys Gly Gly Leu Asn His Gln Val
        290                 295                 300

Thr His His Leu Phe Pro Asn Ile Cys His Ile His Tyr Pro Gln Leu
305                 310                 315                 320

Glu Asn Ile Ile Lys Asp Val Cys Gln Glu Phe Gly Val Glu Tyr Lys
                325                 330                 335

Val Tyr Pro Thr Phe Lys Ala Ala Ile Ala Ser Asn Tyr Arg Trp Leu
                340                 345                 350

Glu Ala Met Gly Lys Ala Ser
            355
```

-continued (2) INFORMATION FOR SEQ ID NO:18:

(i) SEQUENCE CHARACTERISTICS:
        (A) LENGTH: 365 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:18:

```
Met Thr Ser Thr Thr Ser Lys Val Thr Phe Gly Lys Ser Ile Gly Phe
1               5                   10                  15

Arg Lys Glu Leu Asn Arg Arg Val Asn Ala Tyr Leu Glu Ala Glu Asn
            20                  25                  30

Ile Ser Pro Arg Asp Asn Pro Met Tyr Leu Lys Thr Ala Ile Ile
        35                  40                  45

Leu Ala Trp Val Val Ser Ala Trp Thr Phe Val Phe Gly Pro Asp
50                  55                  60

Val Leu Trp Met Lys Leu Leu Gly Cys Ile Val Leu Gly Phe Gly Val
65                  70                  75                  80

Ser Ala Val Gly Phe Asn Ile Ser His Asp Gly Asn His Gly Gly Tyr
                85                  90                  95

Ser Lys Tyr Gln Trp Val Asn Tyr Leu Ser Gly Leu Thr His Asp Ala
            100                 105                 110

Ile Gly Val Ser Ser Tyr Leu Trp Lys Phe Arg His Asn Val Leu His
            115                 120                 125

His Thr Tyr Thr Asn Ile Leu Gly His Asp Val Glu Ile His Gly Asp
    130                 135                 140

Glu Leu Val Arg Met Ser Pro Ser Met Glu Tyr Arg Trp Tyr His Arg
145                 150                 155                 160

Tyr Gln His Trp Phe Ile Trp Phe Val Tyr Pro Phe Ile Pro Tyr Tyr
                165                 170                 175

Trp Ser Ile Ala Asp Val Gln Thr Met Leu Phe Lys Arg Gln Tyr His
            180                 185                 190

Asp His Glu Ile Pro Ser Pro Thr Trp Val Asp Ile Ala Thr Leu Leu
        195                 200                 205

Ala Phe Lys Ala Phe Gly Val Ala Val Phe Leu Ile Ile Pro Ile Ala
    210                 215                 220

Val Gly Tyr Ser Pro Leu Glu Ala Val Ile Gly Ala Ser Ile Val Tyr
225                 230                 235                 240

Met Thr His Gly Leu Val Ala Cys Val Val Phe Met Leu Ala His Val
                245                 250                 255

Ile Glu Pro Ala Glu Phe Leu Asp Pro Asp Asn Leu His Ile Asp Asp
            260                 265                 270

Glu Trp Ala Ile Ala Gln Val Lys Thr Thr Val Asp Phe Ala Pro Asn
        275                 280                 285

Asn Thr Ile Ile Asn Trp Tyr Val Gly Gly Leu Asn Tyr Gln Thr Val
    290                 295                 300

His His Leu Phe Pro His Ile Cys His Ile His Tyr Pro Lys Ile Ala
305                 310                 315                 320

Pro Ile Leu Ala Glu Val Cys Glu Glu Phe Gly Val Asn Tyr Ala Val
                325                 330                 335

His Gln Thr Phe Phe Gly Ala Leu Ala Ala Asn Tyr Ser Trp Leu Lys
            340                 345                 350

Lys Met Ser Ile Asn Pro Glu Thr Lys Ala Ile Glu Gln
```

(2) INFORMATION FOR SEQ ID NO:19:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:19:

CCAAGCTTCT GCAGGAGCTC TTTTTTTTTT TTTTT     35

(2) INFORMATION FOR SEQ ID NO:20:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic oligonucleotide"

(ix) FEATURE:
        (A) NAME/KEY: misc_feature
        (B) LOCATION: 21
        (D) OTHER INFORMATION: /number= 1
            /note= "N=Inosine or Cytosine"

(ix) FEATURE:
        (A) NAME/KEY: misc_feature
        (B) LOCATION: 27
        (D) OTHER INFORMATION: /number= 2
            /note= "N=Inosine or Cytosine"

(xi) SEQUENCE DESCRIPTION: SEQ ID NO:20:

CUACUACUAC UACAYCAYAC NTAYACNAAY AT     32

(2) INFORMATION FOR SEQ ID NO:21:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic oligonucleotide"

(ix) FEATURE:
        (A) NAME/KEY: misc_feature
        (B) LOCATION: 13
        (D) OTHER INFORMATION: /number= 1
            /note= "N=Inosine or Cytosine"

(ix) FEATURE:
        (A) NAME/KEY: misc_feature
        (B) LOCATION: 19
        (D) OTHER INFORMATION: /number= 2
            /note= "N=Inosine or Cytosine"

(xi) SEQUENCE DESCRIPTION: SEQ ID NO:21:

CAUCAUCAUC AUNGGRAANA RRTGRTG     27

(2) INFORMATION FOR SEQ ID NO:22:

(i) SEQUENCE CHARACTERISTICS:
        (A) LENGTH: 33 base pairs
        (B) TYPE: nucleic acid

```
        (C) STRANDEDNESS: single
        (D) TOPOLOGY: linear (ii) MOLECULE TYPE: other nucleic acid (xi) SEQUENCE DESCRIPTION: SEQ ID NO:22:

CUACUACUAC UAGGAGTCCT CTACGGTGTT TTG                                33

(2) INFORMATION FOR SEQ ID NO:23:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:23:

CAUCAUCAUC AUAUGAUGCU CAAGCUGAAA CUG                                33

(2) INFORMATION FOR SEQ ID NO:24:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:24:

Gln Xaa Xaa His His
1               5

(2) INFORMATION FOR SEQ ID NO:25:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:25:

CUACUACUAC UACTCGAGCA AGATGGGAAC GGACCAAGG                          39

(2) INFORMATION FOR SEQ ID NO:26:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:26:

CAUCAUCAUC AUCTCGAGCT ACTCTTCCTT GGGACGGAG                          39

(2) INFORMATION FOR SEQ ID NO:27:

(i) SEQUENCE CHARACTERISTICS:
        (A) LENGTH: 47 base pairs
        (B) TYPE: nucleic acid
        (C) STRANDEDNESS: single
        (D) TOPOLOGY: linear
```

-continued

```
    (ii) MOLECULE TYPE: other nucleic acid (xi) SEQUENCE DESCRIPTION: SEQ ID NO:27:

CUACUACUAC UAUCTAGACT CGAGACCAUG GCUGCUGCUC CAGUGUG                47

(2) INFORMATION FOR SEQ ID NO:28:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:28:

CAUCAUCAUC AUAGGCCUCG AGUUACUGCG CCUUACCCAU                         40
```